United States Patent
Kroll et al.

(10) Patent No.: US 12,258,585 B2
(45) Date of Patent: Mar. 25, 2025

(54) METHODS OF PRODUCING MULTI-LAYERED TUBULAR TISSUE CONSTRUCTS

(71) Applicant: President and Fellows of Harvard College, Cambridge, MA (US)

(72) Inventors: Katharina Theresa Kroll, Somerville, MA (US); Kimberly A. Homan, Somerville, MA (US); Mark A. Skylar-Scott, Brookline, MA (US); Sebastien G. M. Uzel, Cambridge, MA (US); David B. Kolesky, Cambridge, MA (US); Patrick Lustenberger, Herrliberg (CH); Jennifer A. Lewis, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1406 days.

(21) Appl. No.: 16/631,677

(22) PCT Filed: Jul. 20, 2018

(86) PCT No.: PCT/US2018/043042
§ 371 (c)(1),
(2) Date: Jan. 16, 2020

(87) PCT Pub. No.: WO2019/018737
PCT Pub. Date: Jan. 24, 2019

(65) Prior Publication Data
US 2020/0164109 A1 May 28, 2020

Related U.S. Application Data

(60) Provisional application No. 62/535,557, filed on Jul. 21, 2017.

(51) Int. Cl.
| | | |
|---|---|---|
| *C12N 5/071* | (2010.01) | |
| *A61F 2/06* | (2013.01) | |
| *A61L 27/28* | (2006.01) | |
| *A61L 27/36* | (2006.01) | |
| *A61L 27/38* | (2006.01) | |
| *A61L 27/50* | (2006.01) | |
| *B33Y 10/00* | (2015.01) | |
| *B33Y 70/00* | (2020.01) | |
| *B33Y 80/00* | (2015.01) | |
| *C12N 5/077* | (2010.01) | |
| *A61F 2/04* | (2013.01) | |

(52) U.S. Cl.
CPC ............. *C12N 5/0691* (2013.01); *A61F 2/06* (2013.01); *A61L 27/28* (2013.01); *A61L 27/3625* (2013.01); *A61L 27/3629* (2013.01); *A61L 27/3633* (2013.01); *A61L 27/3826* (2013.01); *A61L 27/3882* (2013.01); *A61L 27/3891* (2013.01); *A61L 27/507* (2013.01); *B33Y 10/00* (2014.12); *B33Y 70/00* (2014.12); *B33Y 80/00* (2014.12); *C12N 5/0656* (2013.01); *C12N 5/0661* (2013.01); *C12N 5/069* (2013.01); *C12N 5/0697* (2013.01); *A61F 2002/041* (2013.01); *A61F 2002/043* (2013.01); *A61F 2002/044* (2013.01); *A61F 2002/045* (2013.01); *A61F 2002/046* (2013.01); *A61F 2002/048* (2013.01); *A61F 2002/065* (2013.01); *A61F 2240/001* (2013.01); *A61L 2420/08* (2013.01); *C12N 2513/00* (2013.01); *C12N 2533/54* (2013.01); *C12N 2533/56* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 3,413,387 A | 11/1968 | Ohsol | |
| 2015/0050686 A1 | 2/2015 | Sheth et al. | |
| 2016/0287756 A1 | 10/2016 | Lewis et al. | |
| 2018/0030409 A1 | 1/2018 | Lewis et al. | |
| 2018/0110901 A1 | 4/2018 | Lewis et al. | |
| 2020/0063107 A1* | 2/2020 | Kong | A61F 2/06 |

FOREIGN PATENT DOCUMENTS

| | | |
|---|---|---|
| CN | 101259292 A | 9/2008 |
| CN | 104490489 A | 4/2015 |
| CN | 105561395 A | 5/2016 |
| CN | 106163581 A | 11/2016 |
| KR | 20170006909 A | 1/2017 |
| WO | WO 2014/209994 A2 | 12/2014 |
| WO | WO 2015/069619 A1 | 5/2015 |
| WO | WO 2015/073944 A2 | 5/2015 |
| WO | WO 2016/019087 A1 | 2/2016 |
| WO | WO 2016/141137 A1 | 9/2016 |
| WO | WO 2016/179242 A1 | 11/2016 |
| WO | WO 2018/048900 A1 | 3/2018 |

(Continued)

OTHER PUBLICATIONS

The Decision of Final Rejection of the Application received in Chinese Application No. CN 2018800588931, dated May 31, 2022 (in Chinese and including English translation).

(Continued)

Primary Examiner — Allison M Fox

(74) Attorney, Agent, or Firm — Crowell & Moring LLP

(57) ABSTRACT

Described are methods for producing multi-layered tubular tissue structures, tissue structures produced by the methods, and their use.

25 Claims, 25 Drawing Sheets

(56) References Cited

FOREIGN PATENT DOCUMENTS

| WO | WO 2018/106704 A1 | 6/2018 |
| WO | WO 2018/106705 A1 | 6/2018 |
| WO | WO 2019/018737 A1 | 1/2019 |

OTHER PUBLICATIONS

Communication dated Mar. 19, 2021 and Extended European Search Report dated Mar. 11, 2021 (including Annex to the European Search Report) received in European Patent Application No. 188355903.

First Office Action received in corresponding European Application No. 188355903, dated Feb. 1, 2023.

Second Office Action and Search Report received in the corresponding Chinese Patent Application No. 2018800588931, dated Feb. 23, 2022 (in Chinese and including English translation of Second Office Action).

Examination Report No. 1 for standard patent application received in corresponding Australian Application No. 2018302288, dated Jun. 19, 2023 (3 pages).

First Office Action and Search Report received in the corresponding Chinese Patent Application No. 2018800588931, dated Aug. 9, 2021 (including English translation).

Wu, W., et al., "Omnidirectional Printing of 3D Microvascular Networks," *Adv. Mater.*, 23:H178-H183 (2011).

Cardiff, R.D., et al., "Manual Hematoxylin and Eosin Staining of Mouse Tissue Sections," *Cold Spring Harb Protoc.*, doi:10.1101/pdb.prot073411, 655-658 (2014).

Homan, K.A., et al., "Bioprinting of 3D Convoluted Renal Proximal Tubules on Perfusable Chips," *Sci. Rep.*, 6, 34845, 13 pages (2016).

Kolesky, D.B., et al., "3D Bioprinting of Vascularized, Heterogeneous Cell-Laden Tissue Constructs," *Adv. Mater.*, 26:3124-3130 (2014).

Kolesky, D.B., et al., "Three-dimensional bioprinting of thick vascularized tissues," *PNAS*, 113(12) 3179-3184 (2016).

Lorang, D.J., et al., "Photocurable Liquid Core-Fugitive Shell Printing of Optical Waveguides." *Adv. Mater.*, 23:5055-5058 (2011).

Frutiger, A., et al., "Capacitive Soft Strain Sensors via Multicore-Shell Fiber Printing," *Adv. Mater.*, 272440-2446 (2015).

Notification of Transmittal of the International Search Report and The Written Opinion of the International Searching Authority dated Sep. 26, 2018 and the International Search Report and Written Opinion dated Sep. 26, 2018 received in PCT Application No. PCT/US2018/043042.

Notification Concerning Transmittal of the International Preliminary Report on Patentability dated Jan. 30, 2020 and the International Preliminary Report on Patentability dated Jan. 21, 2020 received in PCT Application No. PCT/US2018/043042.

\* cited by examiner

Core: Pluronic F127, thrombin
Middle shell: Gelatin, fibrinogen, and smooth muscle cells
Outer shell: Gelatin, fibrinogen, and fibroblasts Gelatin might be restraining but the smooth muscle cells exhibit physiological calcium traces

METHODS OF PRODUCING MULTI-LAYERED TUBULAR TISSUE CONSTRUCTS

RELATED APPLICATIONS

The present patent document is a § 371 filing based on PCT Application Serial No. PCT/US2018/043042, filed Jul. 20, 2018, which claims the benefit of the filing date under 35 U.S.C. § 119 (e) of Provisional U.S. Patent Application Ser. No. 62/535,557, filed Jul. 21, 2017, which is hereby incorporated by reference.

FEDERALLY SPONSORED RESEARCH OR DEVELOPMENT

This invention was made with government support under contract number CMMI-1548261 awarded by the National Science Foundation. The government has certain rights in the invention.

BACKGROUND

Described are methods of producing multi-layered tubular tissue constructs.

Blood vessel serve as conduits throughout the body, but their function is not limited to simple nutrient and oxygen transport. They regulate blood pressure, body temperature and electrolyte homeostasis, and have immuno-modulatory function. They can be divided in blood vessel, arterial or venous type. Both arteries and veins have the same three distinct tissue layers, called tunics. The tunics of blood vessels are three layers: an inner, middle, and outer layer that are called, respectively, the tunica intima, the tunica media, and the tunica externa (or tunica adventitia). Between arteries and veins the layer thickness changes with the veins having thinner walls compared to capillaries. Capillaries are comprised of intima and vessel-stabilizing pericytes.

The layers of a blood vessel each serve a distinct biological function. The intima (endothelium) is highly tissue-specific and serves as contact site to the blood stream. It also has regulatory function signaling to the smooth muscle cell layer below. The tunica media is the muscle layer of the vessel with smooth muscle cells, collagen and elastin aligned in a highly organized fashion perpendicular to blood flow direction. Adventitia layer also known as tunica externa is the outermost tunica (layer) of a blood vessel, surrounding the tunica media. It is mainly composed of collagen and, in arteries, is supported by external elastic lamina between tunica media and adventitia. The tunica adventitia serves to anchor the blood vessel to nearby organs, giving it stability.

Small diameter vascular tissue engineering holds great clinical promise in treatment of vascular disease and grafting implants into human hosts. In recent years, extensive progress has been made to move towards clinically relevant models and new techniques to recreate full vascular function. For example, extensive progress has been made to move towards clinically relevant models and new techniques to recreate full vascular function. Efforts have been focused on producing constructs with the right mechanical and immunogenic properties to realize fully transplantable grafts. This has been pursued via various routes, e.g. from entirely synthetic polymers to tissue engineered cell sheets wrapped around a mandrel.

However, many of these techniques require cumbersome and time-consuming procedures to manufacture the necessary components required to recreate human vascular biology and are not necessarily modular. Vascular tissue engineering, also, has focused on producing biomimetic, straight conduits for implantation just the vessel as the tissue of interest. However, in tissue engineering in general, there is a need for bridging an engineered vascular tissue for implantation and host perfusion upon implantation. A suturable access site could mimic the current methods of organ transplantation, where the organ or tissue piece is transplanted with its corresponding vasculature and the blood vessels are used to suture the tissue into the new host facilitating the direct blood perfusion of the transplanted tissue.

As such, there still exists a need for tissue constructs having more complex architecture and ready for use in numerous medical applications, e.g. implantation of a tissue connected to the blood vessel as a suturing site.

SUMMARY

Certain embodiments relate to a method of producing a perfusable multi-layered tubular tissue construct comprising: depositing on a substrate one or more filaments, each filament comprising: a plurality of concentric and coaxial cell-laden ink layers, each cell-laden ink layer comprising one or more predetermined cell types and extending at least a portion of the length of the filament, and within the cell-laden ink layers a core comprising a fugitive ink, wherein the fugitive ink serves as a template for an open perfusable lumen within the filament; removing the fugitive ink to create the open perfusable lumen; and exposing the one or more filaments to fluid perfusion to induce cell proliferation and development thereby producing the perfusable multi-layered tubular tissue construct. The step of depositing on a substrate one or more filaments comprises flowing the fugitive ink through a first extrusion tube, flowing a first cell-laden ink comprising one or more predetermined cell types through a second extrusion tube overlaying the first extrusion tube, the first cell-laden ink flowing around and enclosing the fugitive ink, and flowing a second cell-laden ink comprising one or more predetermined cell types through a third extrusion tube overlaying the second extrusion tube, the second cell-laden ink flowing around and enclosing the first cell-laden ink, thereby forming the core comprising the fugitive ink surrounded by an inner layer comprising a first cell-laden ink layer and an outer layer comprising a second cell-laden ink layer. The method may further comprise providing an extrusion head including the first, second, and third extrusion tubes arranged in a concentric configuration, wherein the extrusion head is moved relative to the substrate during the flowing of the fugitive ink, the first and the second cell-laden inks, the filament being deposited on the substrate in a predetermined configuration. Each cell-laden ink layer may comprise a different type of viable cells. Alternatively, each cell-laden ink layer may comprise overlapping populations of viable cells. In the method, one or more predetermined cell types may be in aggregates or clusters of cells. The cell aggregates or clusters may range in size from about 10 cells/aggregate or cluster to about 1 million cells/aggregate or cluster. In the method, the cells may be selected from the group consisting of smooth muscle cells (vascular, intestinal, or bronchial), mesenchymal cell (fibroblasts, mesenchymal stem cells), pericytes, endothelial cells (vascular or lymph endothelium), and epithelial cells (intestinal epithelial lining, colon epithelial lining, or airway epithelial lining). The first cell-laden layer may comprise smooth muscle cells. The second cell-laden layer may comprise fibroblast cells. The method may further include a step of injecting a suspension of endothelial cells into the open perfusable lumen after the fugitive ink is removed. The injected endothelial cells may form the intimal layer of a blood vessel. The cell-laden ink layers may form a medial layer and an adventitial layer of a blood vessel. The multi-layered tubular construct may be structurally and functionally similar or the same as a blood vessel, or be a blood vessel. In the method, the multi-layered tubular construct may be a branched multi-layered tubular construct. The method may further include at least partially surrounding the one or more filaments with an extracellular matrix composition. The extracellular matrix composition may comprise one or more of gelatin, fibrin, fibrinogen, transglutaminase, thrombin and gelatin methacrylate, collagen, collagen-acrylate of any kind or its cross-linkable version, Matrigel (a solubilized basement membrane matrix secreted by Engelbreth-Holm-Swarm (EHS) mouse sarcoma cells, poly lactic-co-glycolic acid (PLGA), alginate, or chitosan. The method may further include a step of depositing one or more sacrificial filaments on the substrate prior to at least partially surrounding the one or more cell-laden filaments with the extracellular matrix composition to form a sacrificial filament network interpenetrating the one or more cell-laden filaments, each of the sacrificial filaments comprising a fugitive ink. The network may comprise flow channels in fluid communication with the cell-laden filaments for perfusion thereof after removal of the fugitive ink. The cell-laden filaments may comprise one or more functional chemical substances selected from the group consisting of: drugs, small molecules, toxins, proteins, and hormones. Each of the cell-laden ink layers may comprise a cell concentration of from one cell/ml to about 109 cells/ml. The cell concentration may be uniform throughout each of the cell-laden ink layer. In the method, the step of exposing the one or more filaments to fluid perfusion may be under a fluid sheer stress (FSS). The FSS may be pulsed to mimic blood pressure changes during regular heart beats. In the method, the substrate may be plastic or glass. The substrate may be Matrigel. The substrate may be plasma treated or coated with a layer of at least one of Matrigel, poly L-lysine, geltrex, gelatin, fibrin, fibrinogen, fibronectin, nitogen, vitrogen, collagen I, collagen IV, chitosan, alginate, glycosaminoglycans, or any other biomaterial. The cell-laden ink layers all have the same or varying thickness. Each filament may further comprise one or more concentric and coaxial non-cellular fugitive ink layer, wherein the non-cellular fugitive ink layers of the filament comprise one or more materials that impart mechanical stability to the perfusable multi-layered tissue construct. Each filament may further comprise one or more concentric and coaxial layer comprising growth factors.

Another embodiment relates to a perfusable multi-layered tubular tissue construct produced by the method described herein.

A further embodiment relates to the use of the multi-layered tubular tissue construct produced by the methods described herein as an interface with another printed tissue construct, fugitive network, or a body organ that enables a specific tissue function, e.g., for suturing into a body, for maturation in vitro, or implantation.

A further embodiment relates to the use of the multi-layered tubular tissue construct produced by the methods in vascular disease modeling.

A further embodiment relates to the use of the multi-layered tubular tissue construct produced by the methods described herein in drug toxicity studies.

A further embodiment relates to the use of the multi-layered tubular tissue construct produced by the methods described herein in drug screening applications.

A further embodiment relates to the use of the multi-layered tubular tissue construct produced by the methods described herein in regenerative medicine for replacement of at least one of arteries, veins, arterioles, venules, bronchus, bronchiolus, ureter, trachea, esophagus, intestine, colon, lymph duct, milk duct, pancreatic duct, or bile duct.

A further embodiment relates to the use of the multi-layered tubular tissue construct produced by the methods described herein for replacement of tubular structures having concentric and coaxial cell layers within a body.

Yet further embodiment relates to a method of producing a blood vessel construct, comprising depositing on a substrate one or more filaments, each filament comprising: a first cell-laden ink layer and a second cell-laden ink layer, the first and the second cell-laden layers being concentric and extending at least a portion of the length of the filament, the first cell-laden ink layer comprising a smooth-muscle cell (SMC)-containing cell-laden ink and the second cell-laden ink layer comprising a fibroblast-containing cell laden ink, and within the cell-laden ink layers a core comprising a fugitive ink, wherein the fugitive ink serves as a template for an open perfusable lumen within the filament; removing the fugitive ink to create the open perfusable lumen; after removing the fugitive ink, injecting a suspension of endothelial cells into the open perfusable lumen; and exposing the one or more filaments to fluid perfusion to induce cell proliferation and maturation thereby producing the blood vessel construct.

Another embodiment relates to a printed multi-layered tubular construct, comprising one or more filaments, each filament comprising: a plurality of concentric and coaxial cell-laden ink layers, each cell-laden ink layer comprising one or more predetermined cell types and extending at least a portion of the length of the filament, an open perfusable lumen within the one or more filaments; a sacrificial filament network interpenetrating the one or more cell-laden filaments, each of the sacrificial filaments comprising a fugitive ink; and an extracellular matrix composition at least partially surrounding the one or more filaments and the sacrificial filament network. The printed multi-layered tubular construct may be a large scale vessel, an artery, an arteriole, a small-scale vessel, a vein, trachea, bronchus, airway tissue, milk duct, colon, or intestinal section. The printed multi-layered tubular construct may be comparable to an endothelial or epithelial human tissue. Each cell-laden layer may comprise a different type of viable cells. In the printed perfusable multi-layered tubular construct each cell-laden layer may comprise overlapping populations of viable cells. One or more predetermined cell types may be in aggregates or clusters of cells. The cell aggregates or clusters may range in size from about 10 cells/aggregate or cluster to about 1 million cells/aggregate or cluster. In the printed perusable multi-layered tubular construct, the cells may be selected from the group consisting of smooth muscle cells (vascular, intestinal, or bronchial), mesenchymal cell (fibroblasts, mesenchymal stem cells), pericytes, endothelial cells (vascular or lymph endothelium), or epithelial cells (intestinal epithelial lining, colon epithelial lining, airway epithelial lining). In the printed perfusable multi-layered tubular construct, a first cell-laden layer may comprise smooth muscle cells. In the printed perfusable multi-layered tubular construct, a second cell-laden layer may comprise fibroblast cells. The printed multi-layered tubular construct may further comprise endothelial cells in the open perfusable lumen. In the printed perfusable multi-layered tubular construct, the cell-laden layers may form a medial layer and an adventitial layer to form a functional blood vessel. The printed multi-layered tubular construct may be a blood vessel. The printed perfusable multi-layered tubular construct may be a branched multi-layered tubular construct. The one or more filaments may be at least partially surrounded with an extracellular matrix composition, wherein the extracellular matrix composition comprises one or more of gelatin, fibrin, fibrinogen, transglutaminase, thrombin and gelatin methacrylate, collagen, collagen-acrylate (or a cross-linkable version) of any kind, Matrigel, poly lactic-co-glycolic acid (PLGA), alginate, and chitosan. The network may include flow channels in fluid communication with the cell-laden filaments for perfusion thereof. The cell-laden filaments may comprise one or more functional chemical substances selected from the group consisting of: drugs, small molecules, toxins, proteins, growth factors, and hormones. Each of the cell-laden layers may comprise a cell concentration of from one cell/ml to about $10^9$ cells/ml. The cell concentration may be uniform throughout each of the cell-laden layer. The cell-laden layers may all have the same, or varying thickness. In the printed perfusable multi-layered tubular construct at least one or more filaments further may comprise one or more concentric and coaxial non-cellular fugitive ink layer, wherein the non-cellular layers of the one or more filaments comprise one or more materials that can impart mechanical stability to the multi-layered tissue construct. One or more filaments may further comprise one or more concentric and coaxial layer comprising growth factors.

Yet further embodiment relates to a kit comprising the described printed multi-layered tubular construct, hardware for chip assembly, and instructional materials. The hardware includes stainless steel bottom plates, acrylic lids, screws, printed gaskets, tubing components, and perfusion pins. The kit may further comprise analysis tools, such as a live/dead cellular staining protocol and the needed reagents; staining reagents to stain the tissue of interest for common markers of that specific tissue; histological staining components to visualize tissue damage or matrix remodeling; primers and other reagents for PCR applications.

Yet another embodiment related to a kit comprising hardware parts to print the described multi-layered tubular construct, one or more cell culture media, a biomaterial or supporting material, instructional materials, and optionally, multiple cell sources such as primary cells, embryonic stem cells, pluripotent stem cells, or cells differentiated from a stem cell type; cellular aggregates; growth factors and/or small molecules. The biomaterial or supporting material is at least one of gelatin, fibrin, fibrinogen, transglutaminase, thrombin and gelatin methacrylate, collagen, glycosaminoglycans, collagen-acrylate (or a cross-linkable version) of any kind, Matrigel, poly lactic-co-glycolic acid (PLGA), alginate, or chitosan. The kit may further include custom designed nozzles or commercially available nozzles for extrusion-based bioprinting. The kit may also include hardware for chip assembly, such as stainless steel bottom plates, acrylic lids, screws, printed gaskets, tubing components and perfusion pins.

DETAILED DESCRIPTION

Described are methods that utilize 3-dimensional (3-D) bioprinting approach to generate mature, bioactive, and robust tissue structures and tissue patterns with complex architecture. Given its principal compatibility with generating engineered vasculature with complex shapes, this platform technology could serve to create more advanced organ-specific tissue constructs. Examples of applications for the bio-printed tissue constructs using the described method include disease modeling, as a hook-up site for a functional 3D printed tissue constructs comprising a hierarchical network and tissue specific cell types, and for surgical training for microvessel suturing.

Figure 6A:
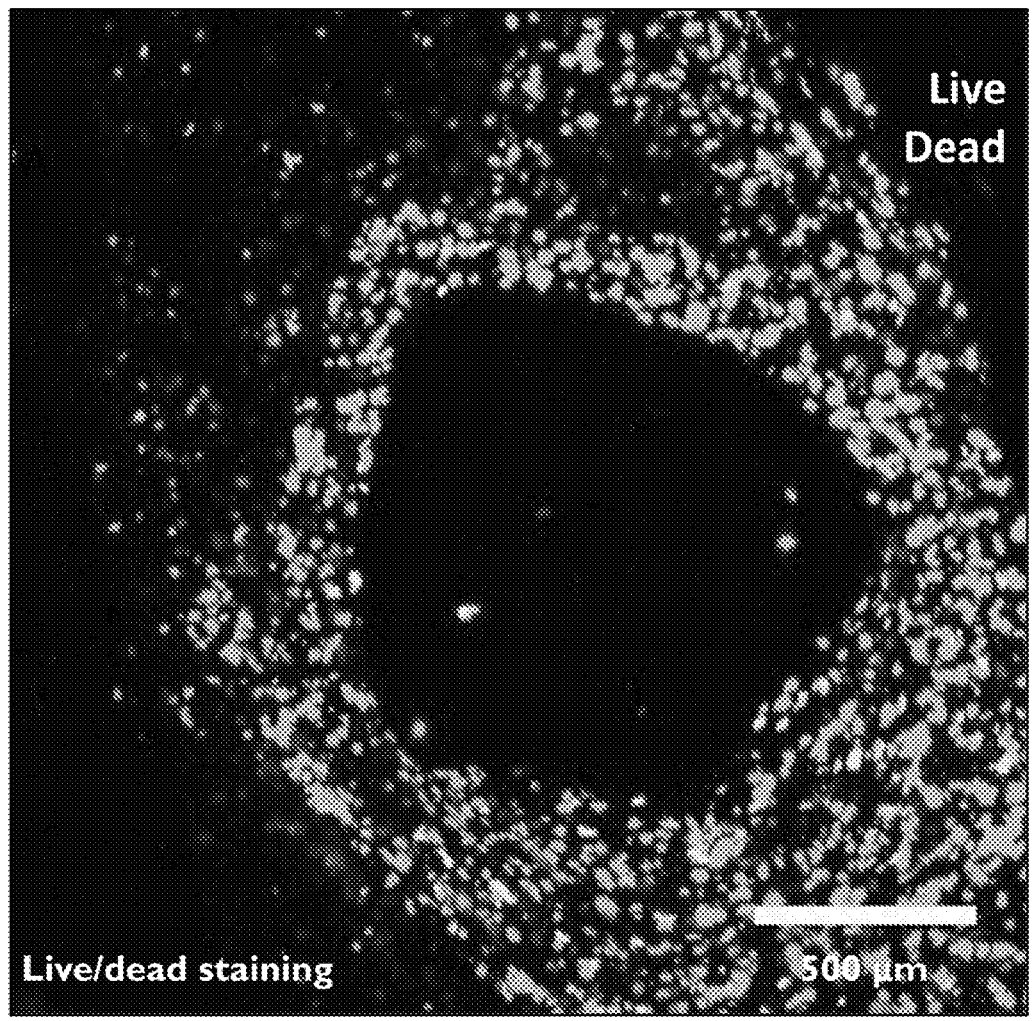
FIG. 6A depicts a representative cell viability confocal microscopy image of live and dead cells stained with a mammalian cell live/dead staining kit (calcein AM and ethidium bromide homodimer).
Figure 6B:
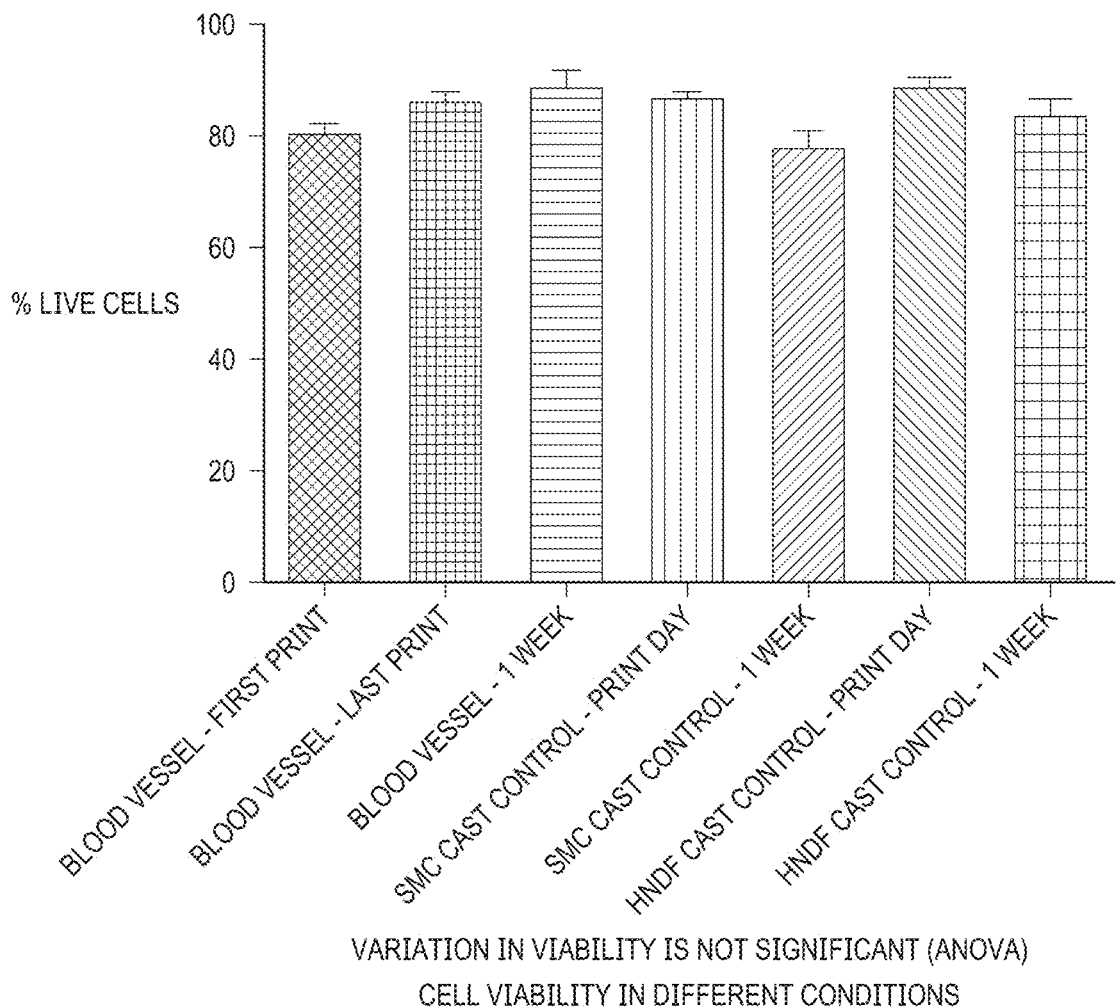
FIG. 6B shows a bar graph of cell viability in different conditions: live/dead cell data obtained from analysis of confocal images (n=6). First and last print were analysed to determine viability during the printing process. This was an exemplary preliminary experiment to determine cellular survival and print technique. Shear stress and perfusion will be adjusted in future experiments to fit more physiological conditions.

Surprisingly, it was shown that, after one week of active perfusion, printed cells are viable and proliferated (FIGS. 6A and 6B). Two weeks of active perfusion revealed first signs of active remodeling of the vessel wall (FIG. 7), with deposition of collagen I, as well as capillary sprouting into the vascular wall tissue (FIGS. 8A-D and FIG. 12). Circular smooth muscle cell alignment was observed at an alignment angle of 45 degrees (FIGS. 8A-D and 9). After four weeks, the vessel was robust enough to sustain a suture and withstand a gravitational force of 0.5 mN (0.5 g) (FIG. 10). Furthermore, importantly, the seeded endothelial cells making up the tunica intima exhibited a proper permeability barrier comparable to their in vivo function as the contact interface to the blood stream (FIG. 13).

PCT Pub. Nos. WO 2015/069619, WO 2016/141137, WO 2016/179242, WO 2016/019087, and WO 2018/048900; U.S. Pub. Nos. US 2016-0287756 A1, US 2018-0030409 A1, and US 2018-0110901 A1, all are hereby incorporated by reference in their entirety.

Also, U.S. Provisional Application Ser. No. 62/431,653, entitled "3D printed core-shell filament and method of printing a core-shell filament," and U.S. Provisional Patent Application Ser. No. 62/431,723, filed Dec. 8, 2016, entitled "Core-shell nozzle for three-dimensional printing and method of use," are hereby incorporated by reference in their entirety.

All patents, patent applications and publications, and other literature references cited herein are hereby incorporated by reference in their entirety. The disclosures of these publications in their entireties are hereby incorporated by reference into this application in order to more fully describe the state of the art as known to those skilled therein as of the date of the invention described and claimed herein.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, compositions, devices and materials are described herein.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a", "and", and "the" include plural references unless the context clearly dictates otherwise. The present disclosure also contemplates other embodiments "comprising," "consisting of" and "consisting essentially of," the embodiments or elements presented herein, whether explicitly set forth or not.

The terms "optional" or "optionally" mean that the subsequently described event, circumstance, or component may but need not occur, and that the description includes instances where the event or circumstance occurs and instances in which it does not.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe a range of values, for example "about 1 to 5" the recitation means "1 to 5" and "about 1 to about 5" and "1 to about 5" and "about 1 to 5," unless specifically limited by context.

Method

The described method relates to a novel three-dimensional bioprinting technique, a fabrication technique that is principally capable of producing biomimetic multi-layered tubular tissue constructs, such as tri-layer blood vessel constructs, of arbitrary geometry. The method results in constructs or architectures with enhanced complexity that are capable of supporting future integration with other tissue engineering strategies, as well as transplantation.

The term "tissue construct," generally, refers to any engineered tissue, such as a blood vessel, or a more complex construct, such as intestine with or without interpenetrating vasculature. In the context of this application, a tissue construct is any multi-layered tubular tissue construct, and includes anywhere from 2 to 8 or more concentric and coaxial cell layers (thereby "multi-layered"). The term "coaxial" means that two or more three-dimensional linear forms (e.g., layers) share a common axis; i.e., the cell layers of the tissue construct share a common axis. The term "concentric" in reference to the cell layers means that the layers have a common center. Exemplary tissue constructs produced by the described methods include, e.g., a large scale vessel, an artery, an arteriole, a small scale vessel, a vein, a venule, trachea, bronchus, bronchi, airway tissue, milk duct, colon, and intestinal section. The construct may be a branched construct. The term "branched" in reference to the tubular tissue construct described herein refers to having two or more branches.

Specifically, in certain embodiments, the described method is for producing a multi-layered tubular tissue construct. The method comprises depositing on a substrate one or more filaments, wherein each deposited filament can comprise a plurality of concentric and coaxial cell-laden ink layers, each cell-laden ink layer comprising one or more predetermined cell types and extending at least a portion of the length of the filament, and, within the cell-laden ink layers, a core comprising a fugitive ink, wherein the fugitive ink serves as a template for an open perfusable lumen within the filament. The method also comprises removing the fugitive ink to create the open perfusable lumen, and exposing the one or more filaments to fluid perfusion to induce cell proliferation and development thereby producing the multi-layered tubular tissue construct.

The term "depositing on a substrate one or more filaments" may be understood as depositing the filaments directly on the substrate or directly on another filament, channel or portion previously deposited or formed on the substrate.

The term depositing also includes embedding, which in reference to "embedding a filament in a substrate, e.g., an extracellular matrix material (ECM)" refers to either placing the filament on top of the substrate, or embedding the filament within the substrate, or printing the filament into the substrate.

In certain embodiments, these cell-laden ink layers of the multi-layered tubular tissue construct described herein may be referred to as a first, a second, a third, etc., cell-laden ink layers or cell-laden layers, where the "first" cell-laden ink layer is the closest to the core of the filament; the "second" cell-laden ink layer is immediately adjacent and surrounding the first cell-laden ink layer; and the "third" cell-laden ink layer is immediately adjacent and surrounding the second and the first cell-laden ink layers, etc.

Figure 1:
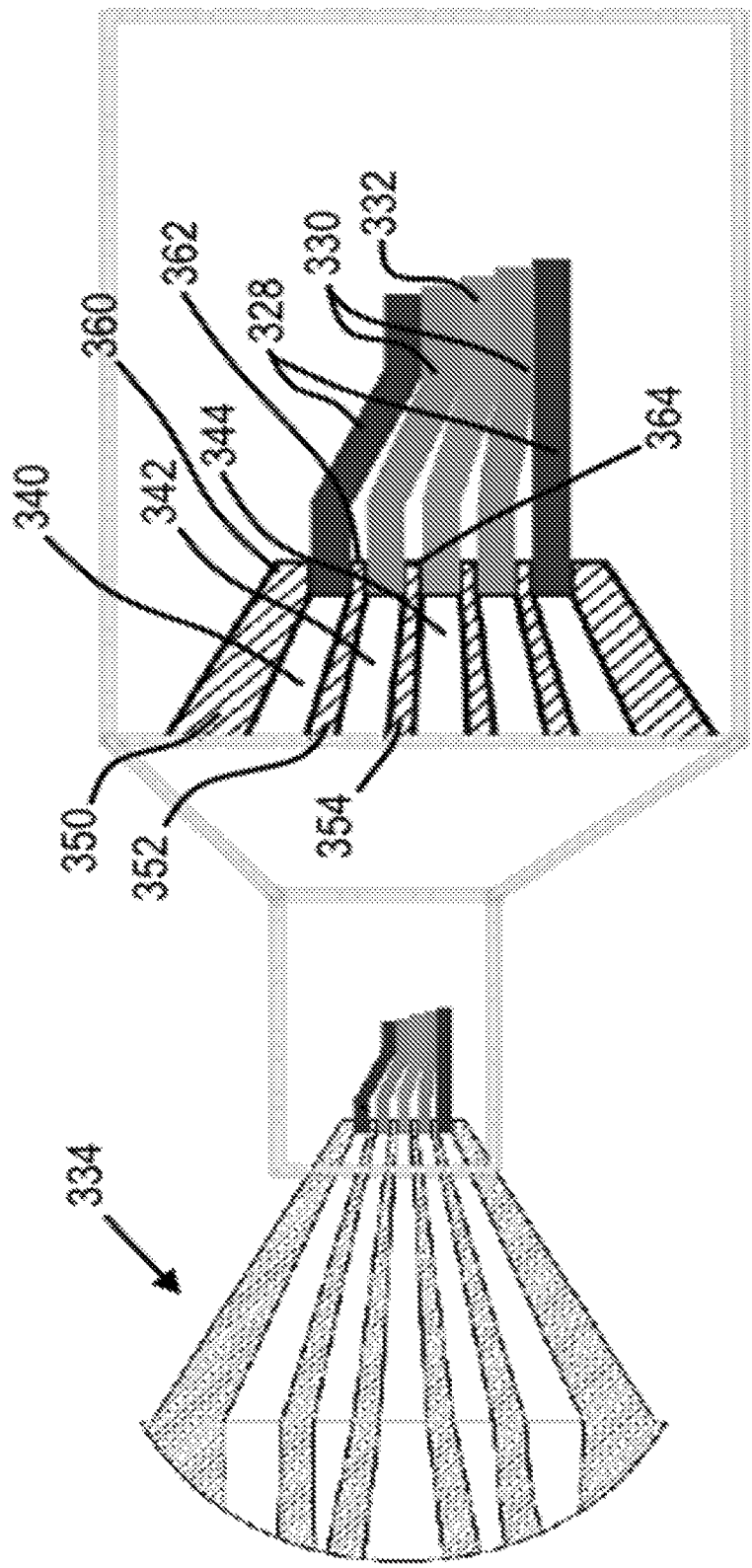
FIG. 1 illustrates an overview of the core-shell printing technology described herein.

In order to produce coaxial and concentric layer structures of tubular body structures, such as a blood vessel, cell layers, e.g., adventitial and medial layer of a blood vessel can be bioprinted using a multicore-shell approach as illustrated in FIG. 1. Exemplary core-shell nozzles that may be used in the bioprinting methods described herein were described in PCT Pub. Nos. WO 2018/106704 and WO 2018/106705, which are incorporated herein in its entirety. For example, the nozzle may include a first nozzle tip defining a first outlet, where the first nozzle tip includes a first channel extending there through. The nozzle may further include a second nozzle tip defining a second outlet, where the second nozzle tip includes a second channel extending there through, and where the first channel surrounds the second outlet. The second nozzle tip may be retracted longitudinally with respect to the first nozzle tip such that the second outlet of the second nozzle tip is located in the first channel.

Specifically, FIG. 1 shows an illustration of an extrusion process from a three-material core-shell nozzle 334. The nozzle 334 may, as shown, have a first channel 344, a second channel 342, and a third channel 340 for respectively extruding a first material 332 (e.g., fugitive ink), and second material 330 (e.g., a first cell-laden ink), and a third material 328 (e.g., a second cell-laden ink). Advantageously, the flow rates of each of the materials may be precisely controlled. For example, the flow rate of the first material through the first channel may be slightly increased, and/or the flow rate of the second material through the second channel may be slightly decreased, etc. The multi-core shell approach was also previously described in PCT Pub. No. WO 2016/019087; and an article by Frutiger et al., *Advanced Materials*, 27:2440-2446 (2015), contents of which are incorporated by reference in their entirety, in reference to producing a soft sensor fiber.

Figure 2:
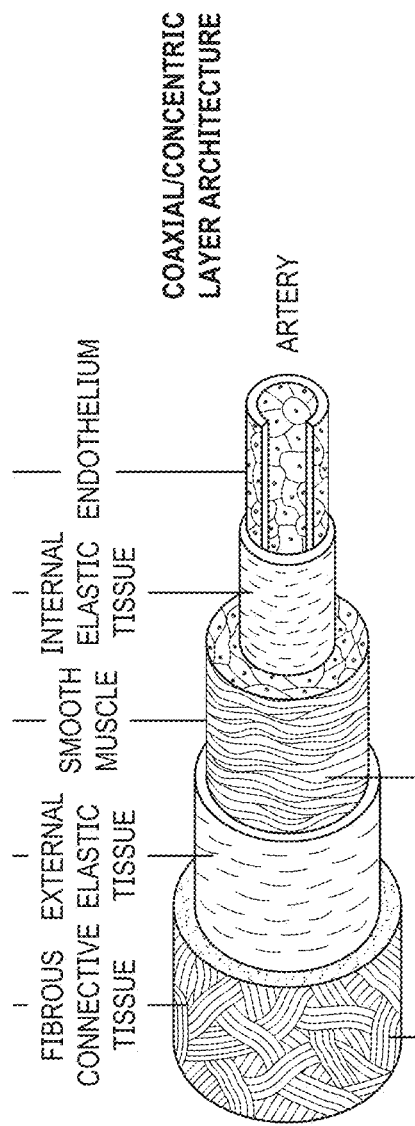
FIG. 2 illustrates an overview of the described method including core-shell printing hydrogels.
Figure 2:
Figure 2:
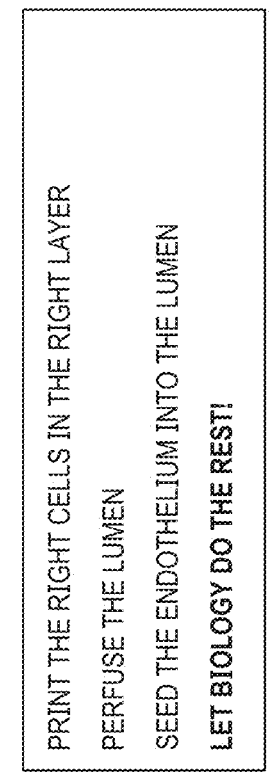
Figure 3:
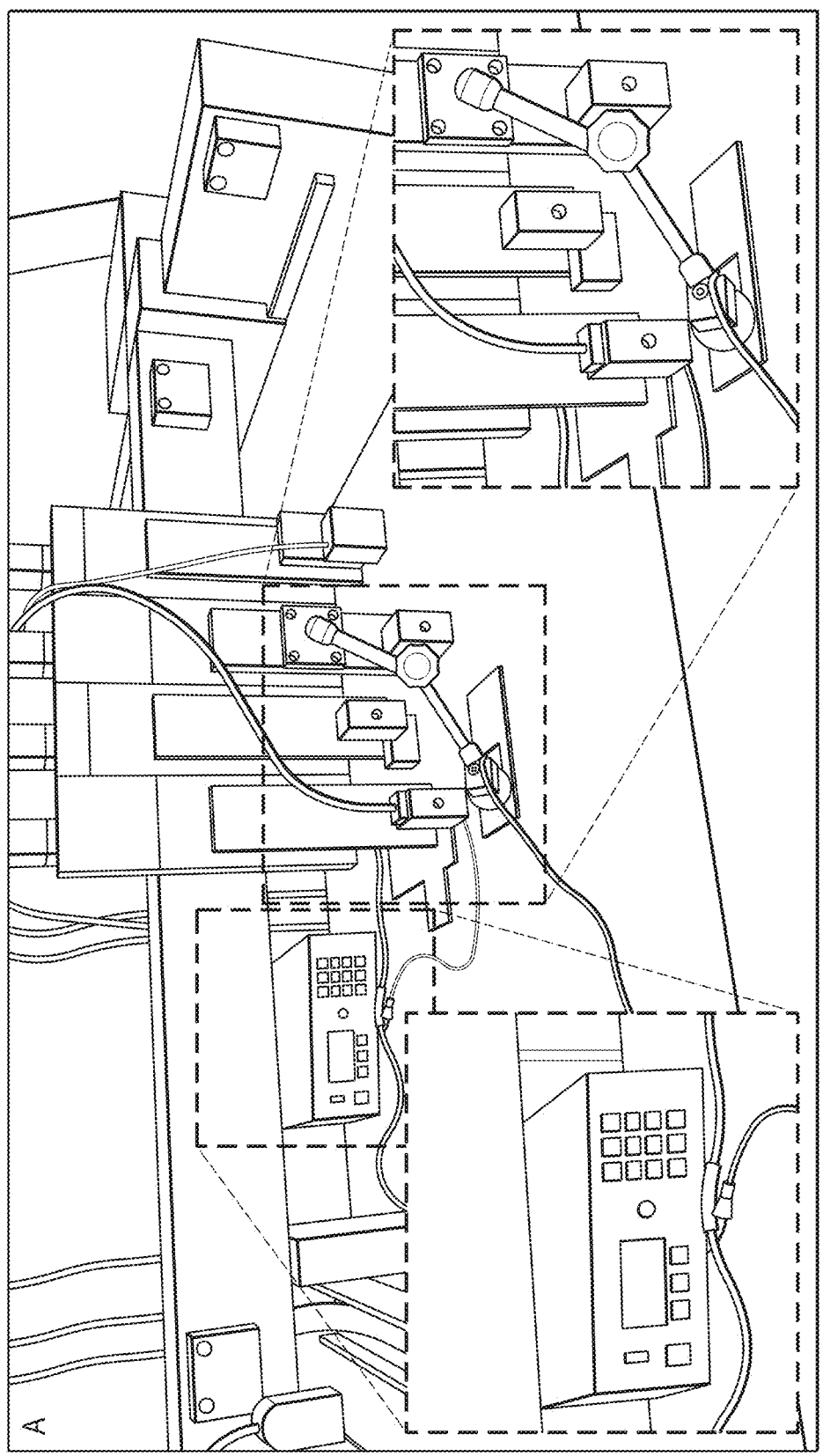
FIG. 3 illustrates a 3D printer and equipment details: (A) Custom-built 3D printer with 4 individually addressable print heads (white arrow, inset on the bottom left). The grey arrow points to one of the compressed air pressure boxes powering the extrusion-based printing method (inset on the bottom right). (B) Image of the multicore-shell nozzle rendered in SolidWorks with the respective nozzle diameters. (C) Image of the printing setup with the cooling system attached to the syringes mounted on the multicore-shell nozzle (arrow). (D) PDMS printed gasket on a glass slide, dimension shown: inner width, inner length.
Figure 3:
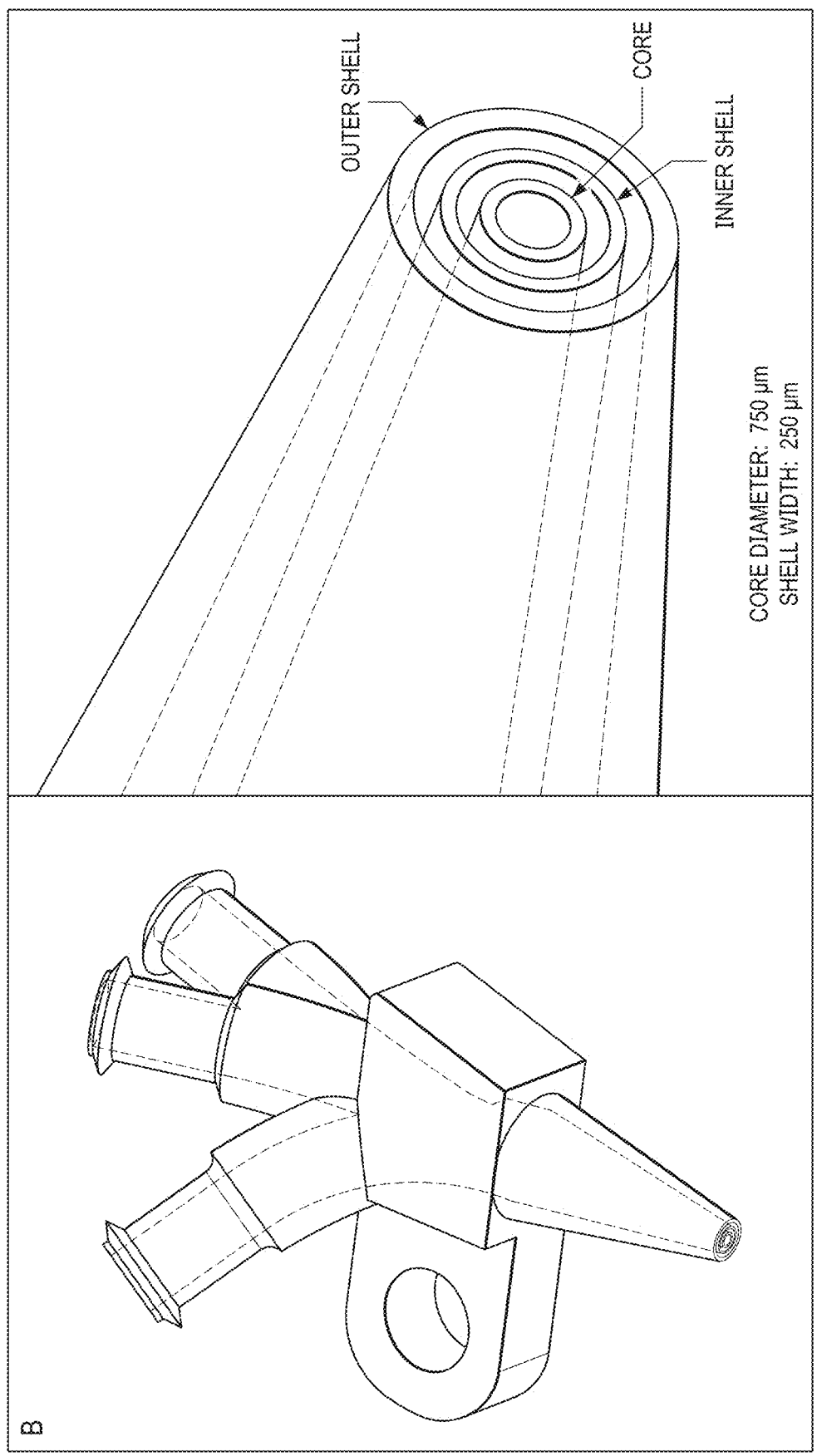
Figure 3:
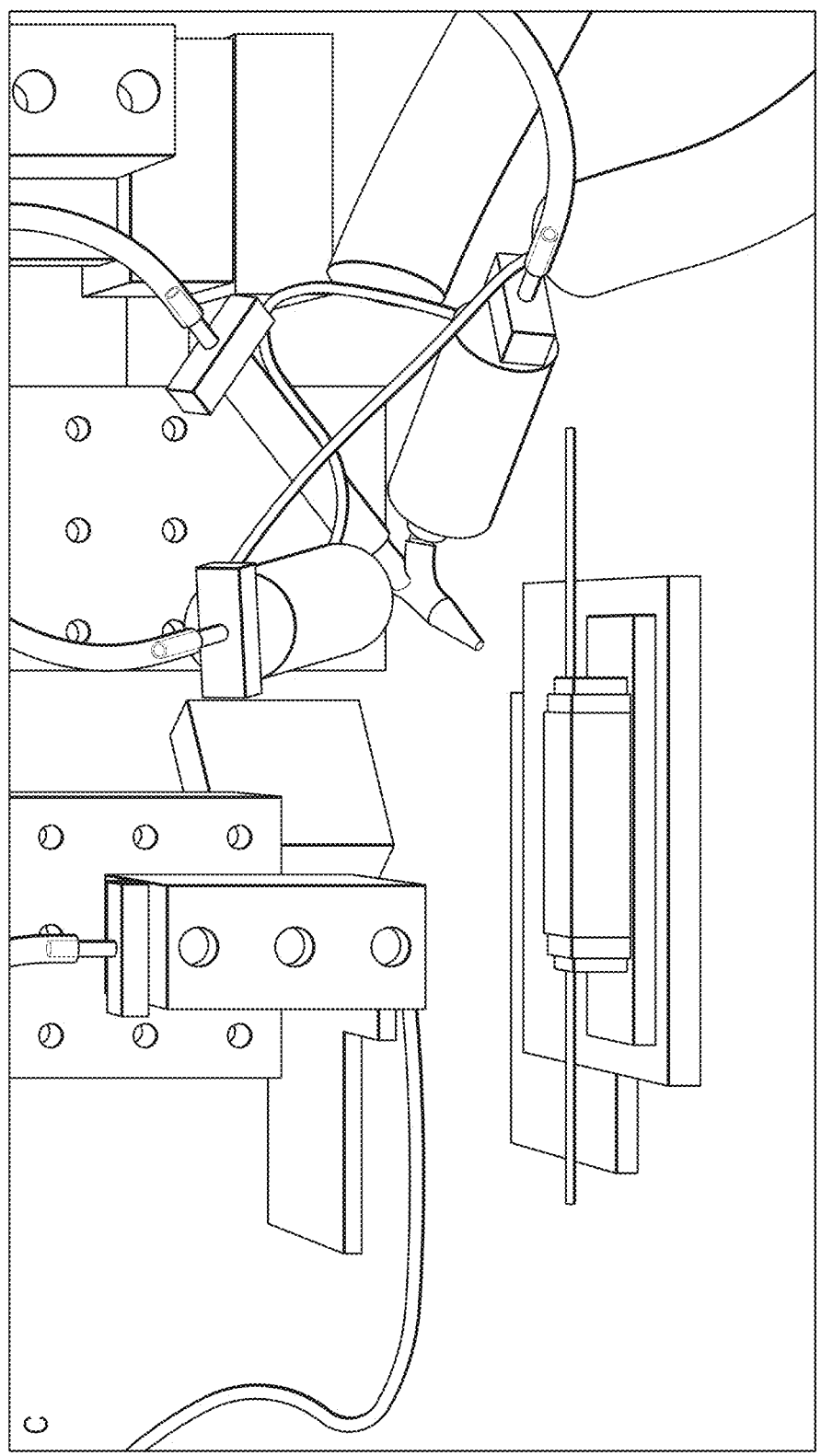
Figure 3:
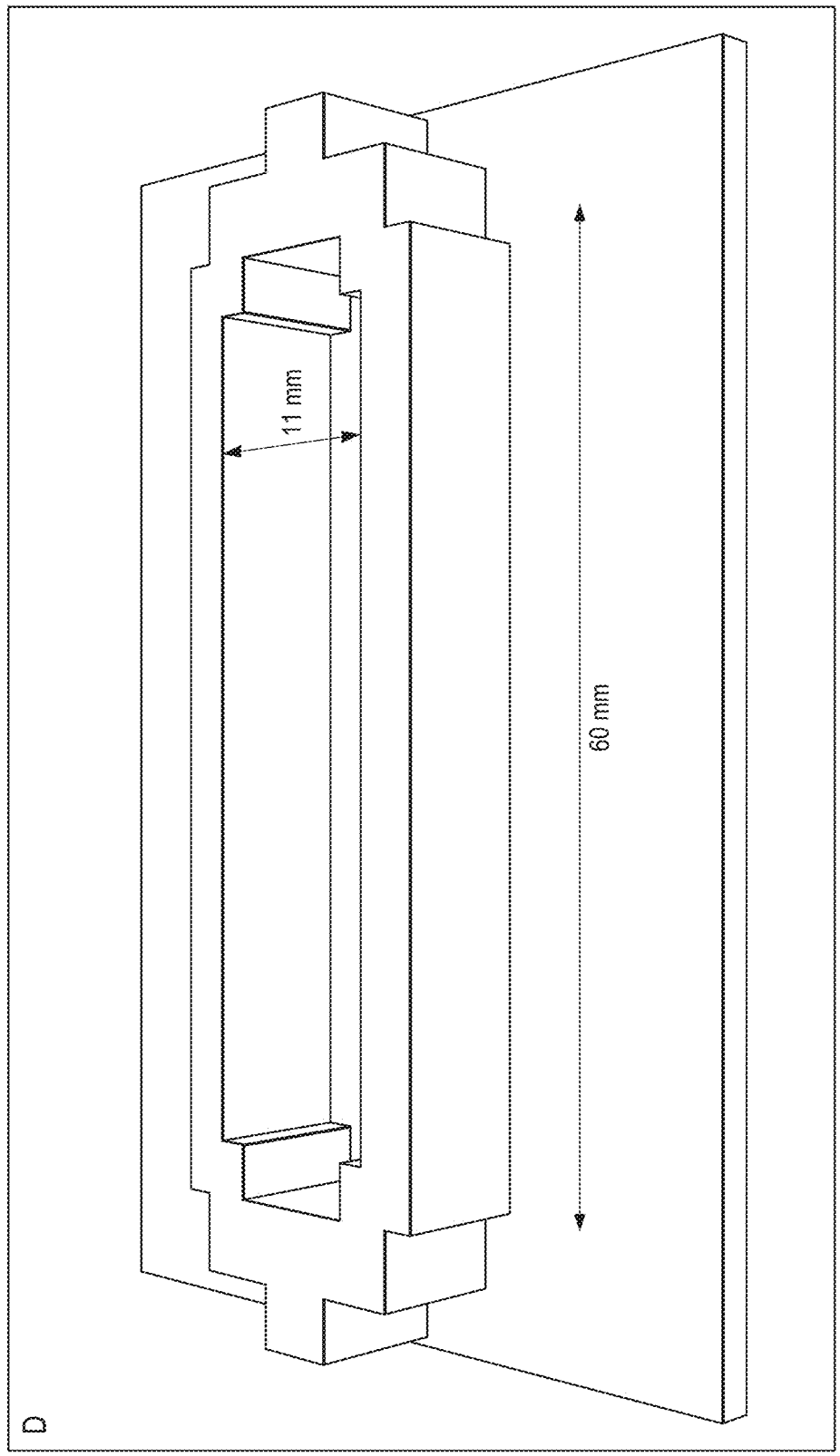

The multicore-shell approach is also illustrated in FIGS. 2 and 3, with cell-laden inks containing predetermined type or types of viable cells, e.g., the layer-specific fibroblasts and smooth muscle cells for the adventitial and medial layer of a blood vessel, respectively. The multicore-shell approach allows for printing multi-layered tubular tissue constructs that are perfusable: the predetermined type or types of viable cells are printed in the pre-determined layer(s), and the construct is perfused and seeded with the endothelial cells.

FIG. 3 shows pictures of an exemplary 3D printer and equipment details for the described methods: (A) shows a picture of a custom-built 3D printer with 4 individually addressable print heads (inset on the bottom left) (A). The dark arrow points to one of the compressed air pressure boxes powering the extrusion-based printing method (inset on the bottom right). Image of the exemplary multicore-shell nozzle rendered in SolidWorks with the respective nozzle diameters is shown in (B). Specifically, in one embodiment, the core diameter may be 750 µm, shell width may be 250 µm.

Image of an exemplary printing setup with the cooling system attached to the syringes mounted on the multicore-shell nozzle is shown in FIG. 3(C).

FIG. 3(D) shows an exemplary PDMS printed gasket on a glass slide for housing the printed construct, dimension shown: inner width (e.g., 11 mm), inner length (e.g., 60 mm).

Figure 4:
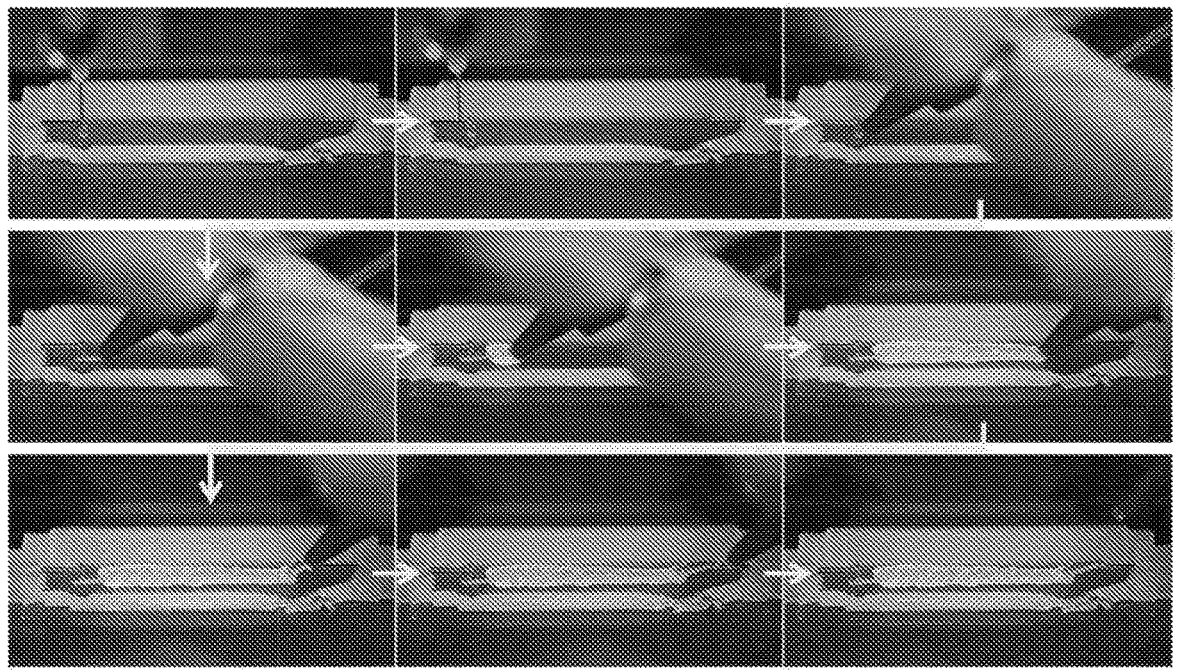
FIG. 4 illustrates 3D bioprinting process: top picture includes still images of a printing video (left to right, top to bottom) with one wall of the PDMS gasket cut away for illustration purposes. First, a fugitive ink pillar is printed and tethered to the inlet perfusion pin. Subsequently, the multicore-shell nozzle is connecting its fugitive ink core to the pillar and starting to extrude the cell-laden inks (red=inner shell, and yellow=outer shell). At the end of the vessel, the fugitive ink core is connected to the outlet perfusion pin and the printing process is finished; and bottom pictures show examples of cross-sections of the tubular printed constructs representing the blood vessel tunics and the possible variations in layer and lumen diameter (the last panel to the right shows the layer integrity after casting the vessel in a surrounding hydrogel matrix).
Figure 4:
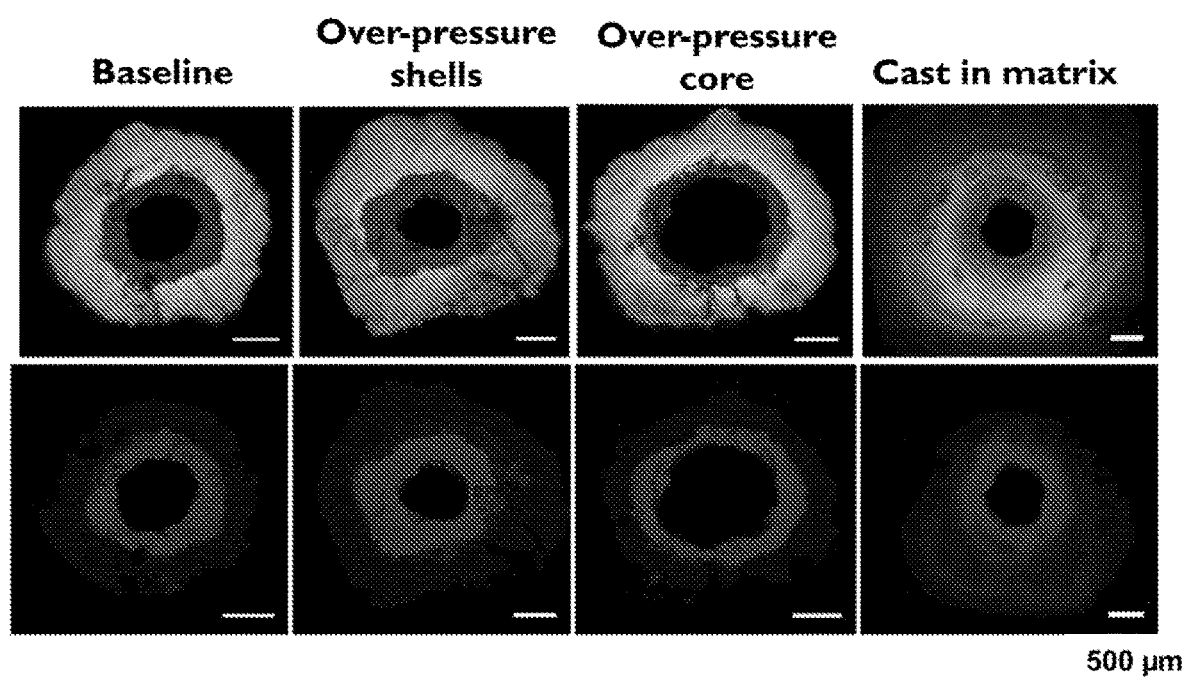

FIG. 4 (top) depicts an exemplary 3D bioprinting printing process as described herein in still images of a printing video (left to right, top to bottom) with one wall of the PDMS gasket cut away for illustration purposes. First, a fugitive ink pillar is printed and tethered to the inlet perfusion pin. Subsequently, the multicore-shell nozzle is connecting its fugitive ink core to the pillar and starting to extrude the cell-laden inks (red=inner shell, and yellow=outer shell). At the end of the vessel, the fugitive ink core is connected to the outlet perfusion pin and the printing process is finished. Cross-sections (bottom of the figure) after printing allow appreciation of the varying layer thickness and lumen diameter that is individually controllable. Furthermore, layer integrity is maintained after casting the filament in a surrounding hydrogel matrix.

As such, in certain embodiments, the step of depositing on a substrate one or more filaments includes: (i) flowing a fugitive ink through a first extrusion tube, (ii) flowing a first cell-laden ink comprising one or more predetermined cell types through a second extrusion tube overlaying the first extrusion tube, the first cell-laden ink flowing around and enclosing the fugitive ink, and (iii) flowing a second cell-laden ink comprising one or more predetermined cell types through a third extrusion tube overlaying the second extrusion tube, the second cell-laden ink flowing around and enclosing the first cell-laden ink. In certain embodiments, additional cell-laden inks may be flowed to create additional cell-laden ink layers to create multi-layered tubular tissue constructs that are perfusable and have 3 or more cell layers. Thereby a core comprising a fugitive ink surrounded by an inner layer comprising a first cell-laden ink (in some embodiments also referred to as "middle shell"), and an outer layer comprising a second cell-laden ink (in some embodiments also referred to as "outer shell"). The term "enclosing" may be understood to mean fully enclosing or partially enclosing (e.g., radially covering), e.g., for producing blood vessels similar to an arteriole. A multi-layered tubular tissue construct comprising a core comprising fugitive ink (wherein the fugitive ink serves as a template for an open perfusable lumen within the filament) surrounded by an inner cell layer(s) and an outer cell layer is thus formed. The term "open perfusable lumen" refers to the lumen or core of the 3D printed filament and tissue construct that is capable of being perfused and capable of being in fluid communication with other tissues/channels, once sutured or implanted. Perfusion of the printed multicore-shell filament as well as additional open channels without wall structure connected to the main multicore-shell filament feeding an adjacent cell population of tissue, like, but not limited to, liver cells or tissue, kidney cells or tissue, and heart cells or tissue. Together with the suturability of the construct implantation of said tissue for functional replacement can be imagined.

In certain embodiments, the method may further include providing an extrusion head (or printhead) including the first, second, third, and optionally fourth and/or fifth extrusion tubes arranged in a concentric configuration, and moving the extrusion head relative to a surface during the flowing of the inks, such that the multi-layered filament is deposited on the surface in a predetermined configuration or pattern. Such a process may be referred to as 3D printing or direct-write printing.

3D printing methods of printing various structures, e.g., a functional part that includes a 3D structure comprising a structural material, and at least one functional electronic device is at least partially embedded in the 3D structure are provided in PCT Pub. No. WO 2014/209994; and a printed stretchable strain sensor are provided in PCT Pub. No. WO 2015/073944, both of which are hereby incorporated by reference in their entirety.

The flowing of the fugitive ink, as discussed above, may occur at a first flow rate f, the flowing of the second cell-laden ink may occur at a second flow rate $f_1$, the flowing of the first cell-laden ink may occur at a third flow rate $f_2$, etc., e.g., where $f_2 > f_1 > f$. In certain alternative embodiments, flowing of the fugitive ink and the cell-laden ink(s) may have an alternative order of the flow rates, e.g., $f_2 > f > f_1$; or $f > f_1 > f$; or $f > f_2 > f_1$; or $f > f_1 > f_2$; or $f_1 > f > f_2$; or $f_1 > f_2 > f$. Typically, each of the flow rates f, $f_1$, and $f_2$ is from about 0.1 L/s to about 10 L/s, although flow rates of up to tens of mL/s or hundreds of mL/s are possible depending on the nozzle size and print speed.

The printhead or extrusion head may move relative to the surface at a print speed of from about 1 mm/s to about 100 mm/s, and more typically from about 1 mm/s to about 10 mm/s. In some cases, the printhead may move relative to the surface at a first print speed and at a second print speed different from the first speed during printing. The first print speed may be lower than the second print speed and may be employed to form ends of the multi-layered filament having increased layer thicknesses.

In certain additional embodiments, the method may also include flowing a third cell-laden ink through a fourth extrusion tube overlying the third extrusion tube, the third cell-laden ink flowing around and enclosing the first cell-laden ink; and so on so forth. As such multiple layers, anywhere from 2 to 8 or more layers that are concentric and coaxial may be created. The various concentric and coaxial layers of the cell-laden filament may or may not be continuous throughout the entire printed filament.

The deposited filaments are formed by utilizing cell-laden inks (e.g., cell-laden inks comprising one or more predetermined cell types, fugitive inks, structural inks, or ECM inks) having a suitable composition and rheological properties. These inks may be viscoelastic and comprise a viscosity with a non-linear shear dependence. The viscosity of the precursor inks may fall in the range of from about 0.001 Pa-sec to about 10,000 Pa-sec. The inks may optionally include viscosifiers or other rheological modifiers to help control the rheological properties. Each cell-laden ink, and optionally, the fugitive and/or ECM ink, may include one or more cells of one or more predetermined cell types in a carrier that may be a liquid or a gel. The carrier may include, in addition to an extracellular matrix material as described above, one or more functional chemical substances as described above. The carrier may also or alternatively include a cell culture medium designed to support the growth of cells. In one example, to form a cell-laden ink comprising viable cells mixed with a hydrogel, a predetermined amount of a hydrogel precursor powder is mixed with a cell culture medium to form a solution of an appropriate composition. The cells of interest are then dispersed in the solution at the desired cell concentration (e.g., any of the cell concentrations set forth above for the cell-laden filaments), and mixed thoroughly. Steps to prepare exemplary cell-laden GelMA inks, cell-laden gelatin-fibrin inks, Pluronic F127 fugitive inks, and PDMS structural inks are described in the Examples below.

In certain embodiments, each cell-laden ink and the resulting cell-laden ink layer can include a different type or types of viable cells. For example, the first cell-laden ink may include Cell Type A and the second cell-laden ink may include Cell Type B; or the first cell-laden ink may include a combination of Cell Types A and C and the second cell-laden ink may include a combination of Cell Types B and E. Alternatively, in some embodiments, certain types of cells may be overlapping in the resulting cell-laden ink layers. For example, the first cell-laden ink may include Cell Type A and B, where the second cell-laden ink may include Cell Type B and C. This would result in the first cell-laden ink layer having Cell Type A and B, and the second cell-laden ink layer having Cell Type B and C (Cell Type B being present in both cell-laden inks and layers).

Each of the one or more cell-laden ink layers can include at least one viable cell and may include a large number of viable cells. For example, each of the cell-laden ink layers may have a cell concentration of at least about 100 cells/ml, at least about 1000 cells/ml, at least about $10^4$ cells/ml, at least about $10^5$ cells/ml, at least about $10^6$ cells/ml, at least about $10^7$ cells/ml, or at least about $10^8$ cells/ml. Typically, the cell concentration is no higher than about $10^9$ cells/ml, or no higher than about $10^8$ cells/ml.

The cell concentration may be uniform or substantially uniform (e.g., within ±10%, within ±5%, or within ±1%) throughout each of the cell-laden layer, and the cell concentration may also be substantially uniform throughout each of the deposited filament.

Alternatively, it is possible to deposit cell-laden layers and filaments that include aggregates or clusters of cells that may range in size from about 10 cells/cluster to about 1 million cells/cluster; or from about 10 cells/cluster to about 10000 cells/cluster, or from about 10 cells/cluster to about 100 cells/cluster. Such clusters may be dispersed uniformly or non-uniformly within the cell-laden layers and filaments (FIG. 15).

Overall, the cell concentration may be substantially uniform throughout the tissue construct, or the cell concentration may include predetermined inhomogeneities within the tissue construct that may be defined by the location and morphology of the tissue construct, and/or by the cell distribution within the tissue construct. The cell clusters can be primary isolated clusters of parenchyma, like beta islets or exocrine part of the pancreas or liver tissue pieces; organoids formed of primary isolated single cells, like liver organoids or intestinal organoids; organoids differentiated from embryonic or induced-pluripotent stem cells, such as kidney organoids; aggregates of stem cells called embryoid bodies; aggregates of primary cells and/or cell lines, e.g. endothelial cell/fibroblast aggregates, cancer spheroids, B-cell zones from lymphnodes.

Figure 15:
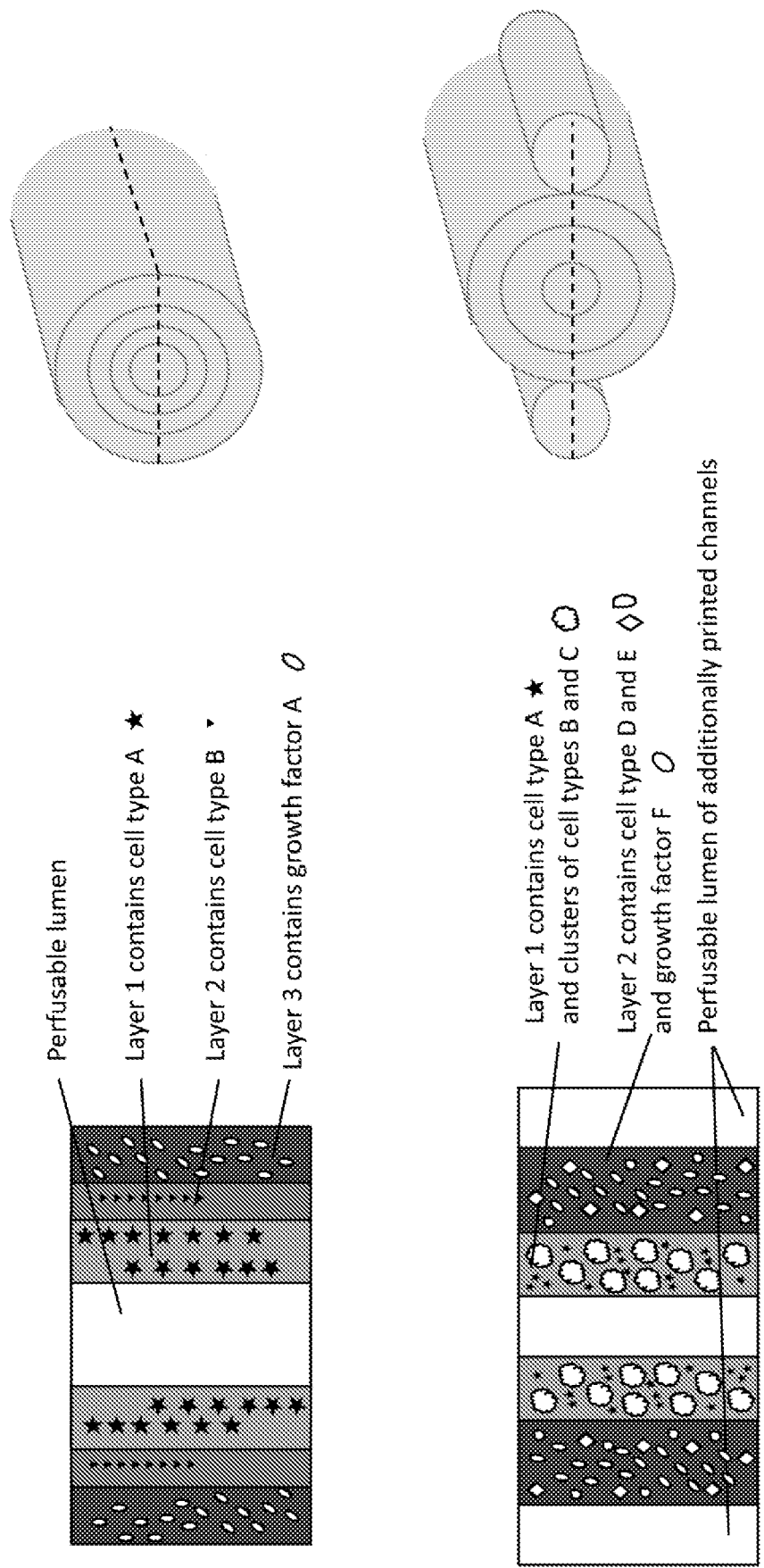
FIG. 15 depicts schematic illustration of longitudinal cross-sections through printed filaments that include cell aggregates or clusters of cells.

In certain embodiments, each cell-laden ink layer comprises both cell clusters of a single or multiple cell types and single cells dispersed within the ink materials of one or more cell types (FIG. 15).

In certain embodiments, each of the cell-laden ink layers comprises a cell concentration of from one cell/ml to about $10^9$ cells/ml.

The viable cells and the predetermined cell types in the multi-layered tubular tissue construct may include any mammalian cell type selected from cells that make up the mammalian body, including germ cells, somatic cells, and stem cells. The cells may be patient-derived. Depending on the type of cell, cells that make up the mammalian body can be derived from one of the three primary germ cell layers in the very early embryo: endoderm, ectoderm or mesoderm. The term "germ cells" refers to any line of cells that give rise to gametes (eggs and sperm). The term "somatic cells" refers to any biological cells forming the body of a multicellular organism; any cell other than a gamete, germ cell, gametocyte or undifferentiated stem cell. For example, in mammals, somatic cells make up all the internal organs, skin, bones, blood and connective tissue. As such, a cell may include any somatic cell isolated from mammalian tissue, including organs, skin, bones, blood and connective tissue (i.e., stromal cells). Examples of somatic cells include fibroblasts, chondrocytes, osteoblasts, tendon cells, mast cells, wandering cells, immune cells, pericytes, inflammatory cells, endothelial cells, myocytes (cardiac, skeletal and smooth muscle cells), adipocytes (i.e., lipocytes or fat cells), parenchyma cells (neurons and glial cells, nephron cells, hepatocytes, pancreatic cells, lung parenchyma cells) and non-parenchymal cells (e.g., sinusoidal hepatic endothelial cells, Kupffer cells and hepatic stellate cells). The term "stem cells" refers to cells that have the ability to divide for indefinite periods and to give rise to virtually all of the tissues of the mammalian body, including specialized cells. The stem cells include pluripotent cells, which upon undergoing further specialization become multipotent progenitor cells that can give rise to functional or somatic cells. Examples of stem and progenitor cells include hematopoietic stem cells (adult stem cells; i.e., hemocytoblasts) from the bone marrow that give rise to red blood cells, white blood cells, and platelets; mesenchymal stem cells (adult stem cells) from the bone marrow that give rise to stromal cells, fat cells, and types of bone cells; epithelial stem cells (progenitor cells) that give rise to the various types of skin cells; neural stem cells and neural progenitor cells that give rise to neuronal and glial cells; and muscle satellite cells (progenitor cells) that contribute to differentiated muscle tissue. In certain embodiments, the cell type or types used as components in the cell-laden ink or printed or placed adjacent to the printed perfusable multilayered or single layered filaments can be pre-aggregated into organoids, spheroids, embryoid bodies, or more general cellular aggregates.

In certain preferred embodiments, the cells may be, but are not limited to smooth muscle cells (vascular, intestinal, or bronchial), mesenchymal cell (fibroblasts, mesenchymal stem cells), endothelial cells (vascular or lymph endothelium), epithelial cells (intestinal epithelial lining, airway epithelial lining), and pericytes or stromal cells.

While the embodiments described herein and figures show a multi-layered tubular structure that takes the shape of a fiber or filament having a round or oval cross-section, the structure can also be fabricated to include a polygonal (e.g., square or rectangular) cross-section, and individual layers can be provided with either rounded or polygonal (e.g., square or rectangular) shaped cross-sections by using tubes that have the desired cross-sectional shape. More complex cross-sectional shapes can also be provided.

In certain embodiments, the cell-laden ink layers all have the same thickness. Alternatively, the cell-laden ink layers all have varying thickness.

In certain embodiments, one or more sacrificial filaments comprising the same or different (i.e., "second" fugitive ink) fugitive ink may be deposited on a substrate to form a sacrificial filament network that interpenetrates one or more multi-layered cell-laden filaments. The network may include a two- or three-dimensional interconnected arrangement or network of the one or more sacrificial filaments. Removal of the fugitive ink after partial or complete encapsulation with the extracellular matrix composition creates a perfusable network of channels in the tissue construct. The perfusable system may serve as perfusion of, e.g. nutrients, but also allow for drainage of fluids of interest. Because, like the multi-layered cell-laden filaments, the sacrificial filaments may be deposited in a 3D printing process that involves extrusion through a micronozzle, it may be advantageous for the fugitive ink to: (1) exhibit shear thinning behavior; (2) exhibit a defined yield stress $\tau_y$; and/or (3) have a shear elastic modulus G' and a shear viscous modulus G" modulus where G'>G" at room temperature.

After printing, the fugitive ink is removed from the core of the filaments to create an open perfusable lumen(s). This can occur before, during, or after encapsulation of the filaments, and optionally the sacrificial filaments in an extracellular matrix. The fugitive ink may be removed by methods described below.

Specifically, before, during, or after encapsulation of the filaments, and optionally the sacrificial filaments, the fugitive ink may be removed to generate open perfusable lumen(s). The fugitive ink may comprise a biocompatible material and may be designed for compatibility with the cell-laden formulations and the extracellular matrix composition during room temperature deposition. Suitable fugitive inks may include, for example, Pluronic F127, Pluronic F123, agarose, sugar, wax, gelatin and fatty oils (e.g., animal fat derived oils such as Crisco). If a hydrogel is employed for the extracellular matrix composition (and/or the extracellular matrix material), and a hydrogel such as Pluronic F127 is employed as the fugitive ink, it may be advantageous for the fugitive ink and the matrix hydrogel to have similar water contents (e.g., within ±30%) to avoid distortion of the fugitive ink after printing. The fugitive ink and the extracellular matrix composition may also be selected to have complementary thermal transitions, as discussed further below.

Pluronic F127 is an FDA-approved material that is biologically inert to multiple cell types over the short time periods needed to complete the fabrication process. The material includes a hydrophobic poly(propylene oxide) (PPO) segment and two hydrophilic poly(ethylene oxide) (PEO) segments arranged in a PEO-PPO-PEO configuration. Pluronic F127 undergoes thermally reversible gelation above a critical micelle concentration (CMC; about 21 wt. %) and the gelation temperature. The gelation temperature decreases from approximately 10° C. to 4° C. as the PEO-PPO-PEO concentration increases. When both of these critical parameters are exceeded, micelles form as the hydrophilic PEO segments self-assemble into corona that are well solvated by water, while the hydrophobic PPO segments tightly associate within the micelle cores. However, below the gelation temperature, the hydrophobic PPO units are hydrated, such that individual PEO-PPO-PEO species become soluble in water giving rise to a gel-to-fluid transition for systems whose concentration exceeds the CMC. Thus, the material liquefies upon cooling below the gel point.

In one example, the extracellular matrix material and/or the extracellular matrix composition may comprise a gel. An ideal gel for bioprinting applications may exhibit a rapid transition from a low viscosity solution to a solid-like gel, which may be seen by an initial increase in shear elastic modulus. Rapid, controllable gelation may enhance printed structure fidelity by minimizing or obviating swelling and dissociation typical of slow gelation processes. The term "gel" may refer to a semi-solid substance that may comprise a gelling agent to provide viscosity or stiffness. The gel may be formed upon use of a gelling agent, such as a thickening agent, crosslinking agent or a polymerization agent, and may comprise a cross-linked structure or a non-cross-linked structure. The gel may be hydrophobic or hydrophilic. Some examples of suitable gels include a hydrogel, thermo-reversible gel, a photo-sensitive gel, a pH sensitive gel, a peptide gel, or a cell type specific gel. Additional examples of gels include silica gel, silicone gel, aloe vera gel, agarose gel, nafion, polyurethane, elastomers (thermoplastic, mineral-oil thermoplastic, etc.), ion-exchange beads, organogels, xerogels and hydrocolloids. Hydrogels include those derived from collagen, hyaluronate, fibrin, alginate, agarose, chitosan, gelatin, Matrigel, glycosaminoglycans, and combinations thereof. In one example, the gel may comprise gelatin methacrylate (GelMA), which is denatured collagen that is modified with photopolymerizable methacrylate (MA) groups. Suitable hydrogels may comprise a synthetic polymer. In certain embodiments, hydrogels may include those derived from poly(acrylic acid) and derivatives thereof, poly(ethylene oxide) and copolymers thereof, poly(vinyl alcohol), polyphosphazene, and combinations thereof. The extracellular matrix material and/or the extracellular matrix composition may comprise a naturally derived biocompatible material, such as one or more extracellular matrix components, including collagen, fibronectin, laminin, hyaluronates, elastin, and/or proteoglycans. Other suitable biocompatible materials for the extracellular matrix material and/or the extracellular matrix composition may include variations of cellulose, Matrigel, acrylates, acrylamides, polylactic co-glycolic acid, epoxies, aldehydes, ureas, alcohols, polyesters, silk, proteins, glycosaminoglycans, carbohydrates, minerals, salts, clays, hydroxyapatite, and/or calcium phosphate.

In certain embodiments, the extracellular matrix material and/or the extracellular matrix composition may comprise gelatin and fibrin. The gelatin and fibrin may form an interpenetrating polymer network that mimics natural extracellular matrix (ECM) and may be optimized for cell attachment, bioprinting, transparency, and biocompatibility. The fibrin-gelatin interpenetrating polymer network may be created by mixing solutions of fibrinogen and gelatin with transglutaminase (TG), a slow-acting $Ca^{2+}$ dependent enzyme, to create a gel-precursor solution that may later be mixed with bovine thrombin to create a fibrin gel backbone. Fibrin may be made from a concentrated fibrinogen solution that has been activated by bovine thrombin and calcium chloride. Fibrin is a rapidly coagulating phase that permits rapid, controllable gelation of a printed structure. Advantageously, fibrin and gelatin can be welded together via mobile surface chain entanglement, while forming a strong interface. Creating monolithic gels of this nature is possible due to the slow crosslinking kinetics of transglutaminase (TG). Although thrombin rapidly induces fibrin gel formation, the gelatin present in the IPN allows one to print sacrificial ink on the already cast layer, and, ultimately, to encapsulate with liquid gelatin-fibrin. The two phases may be weld together, creating a monolithic gel. This material system, which is discussed further below in the Examples, can be readily tailored to modify gelation kinetics, interface adhesion, mechanical properties, optical properties, and cell-material interactions.

In certain embodiments, the extracellular matrix composition comprises one or more of gelatin, fibrin, fibrinogen, transglutaminase, thrombin and gelatin methacrylate, collagen, collagen-acrylate (or a cross-linkable version) of any kind, Matrigel, poly lactic-co-glycolic acid (PLGA), alginate, chitosan.

It is important that the multi-layered cell-laden filaments and surrounding extracellular matrix composition are not damaged during deposition of the sacrificial filaments or removal of the fugitive ink, and thus it is preferred that harsh solvents and/or elevated temperatures are not utilized during the removal process. With proper selection of the fugitive ink and the extracellular matrix composition/material, the fugitive ink may be removed without damage to the tissue construct. For example, if the fugitive ink undergoes a gel-to-fluid transition as described above, cooling of the vascular pattern after encapsulation may be effective for removal of the fugitive ink. To remove Pluronic F127, the construct may be cooled to a temperature of no more than about 1° C., depending on the concentration. It is also contemplated that the fugitive ink may be dissolved in a suitable aqueous solution for removal. Once the fugitive ink is liquefied or dissolved, a vacuum may be applied to an exposed end of the vascular pattern to extract the ink. Alternatively, cell culture medium can be used to wash out the liquefied fugitive ink.

Next, the one or more filaments are exposed to fluid perfusion to induce cell proliferation and development, thereby producing a functional perusable multi-layered tubular tissue construct. In certain embodiments, the step of exposing the one or more filaments to fluid perfusion is under a fluid sheer stress (FSS). The FSS may be pulsed to mimic blood pressure changes during regular heartbeats. Fluid flow is an essential feature of every microsystem involving cell handling, culture or sorting. Flows inevitably generates FSS. "Fluid shear stress" of "FSS" refer to the stress coplanar component along with a cross section of a material. This occurs due to the component's force vector that is analogous to the cross section. It is in contradiction to normal stress that arises from force vectors that are perpendicular to the material's cross section, where it acts. The fluid perfusion may be at FSS anywhere from about 0.000001 dyn/cm$^2$ to about 100 dyn/cm$^2$; alternatively, the fluid perfusion may be at FSS from about 0.01 dyn/cm$^2$ to about 10 dyn/cm$^2$. The exposure to FSS may be constant and can be anywhere from 1 day to 100 days. Methods for producing tissue constructs using FSS were previously described in U.S. Provisional Patent Application Ser. No. 62/517,536, which is incorporated herein in its entirety.

In certain embodiments, after the fugitive ink is removed, additional cells or cell clusters may be deposited or seeded into the lumen generated by removal of a fugitive ink from the filament core. For example, in the context of a blood vessel, the intimal endothelial layer of the vessel is introduced by seeding endothelial cells into the core of the tissue construct. The cells may be seeded by injection of the cells into the open perfusable lumen. Specifically, endothelialization may be effected by injecting a suspension of viable cells (e.g., endothelial cells) into the core of the cell-laden filament(s) after removing the fugitive ink. Using this approach, an endothelial layer having up to 100% confluency may be formed lining the wall of the core, where "100% confluency" means that the wall is completely covered by endothelial cells. Each endothelial layer formed in cell-laden filament may have a confluency of at least about 80%, at least about 90%, at least about 95%, at least about 98%, at least about 99%, or 100%, or any confluency in between 80% and 100%, so that the filament may form a perfusable and functional structure, such as an actual blood vessel.

Figure 12:
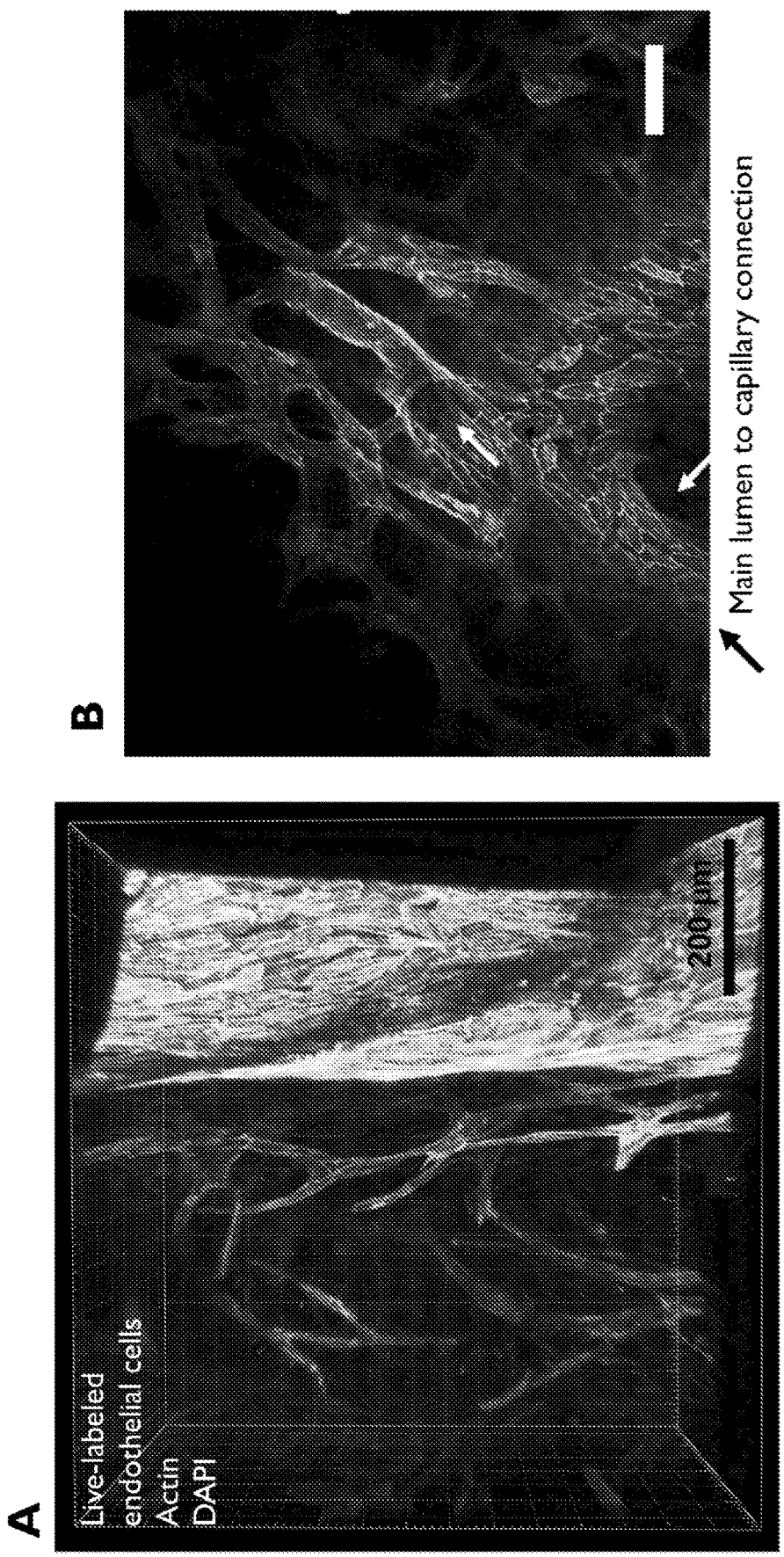
FIG. 12 depicts the vascular wall being supplied with nutrients by a capillary network called vasa vasorum (Latin: vessels of the vessel) in vitro. These smaller capillaries sprout off the main vessel and form a capillary network. By live perfusion of a dye through the lumen of the main printed vessel, we can label the extensive network of small capillary-like vessels into the printed vessel's wall (cyan), that has been developing naturally over the course of 2 weeks of active perfusion with cell culture medium: (A) 3D reconstruction of the main vessel (bright cyan to the right of the image) and the vasa vasorum network in the surrounding layers (cyan network to the left), and (B) luminal view via confocal microscopy of the vasa vasorum network with discrete connections of the main lumen to the capillary network (white arrows).
Figure 13:
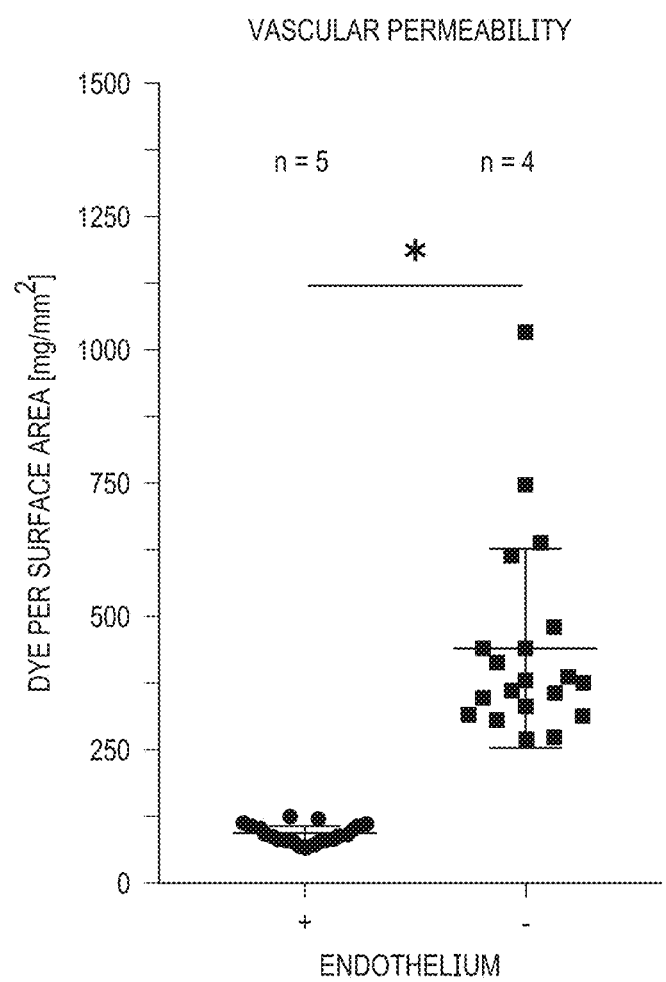
FIG. 13 depicts data showing endothelial permeability of the tested samples similar to in vivo samples via a modified Miles assay.
Figure 13:

In certain embodiments, the injected cells may grow into different layers, e.g., the endothelial cells can start vascularizing the wall of the blood vessel as they do in vivo (see FIG. 12). The endothelial cells might grow into the walls, vascularizing the tubular construct wall upon cues from the surrounding cells with a dense capillary vasculature network connected to the lumen.

Figure 8A:
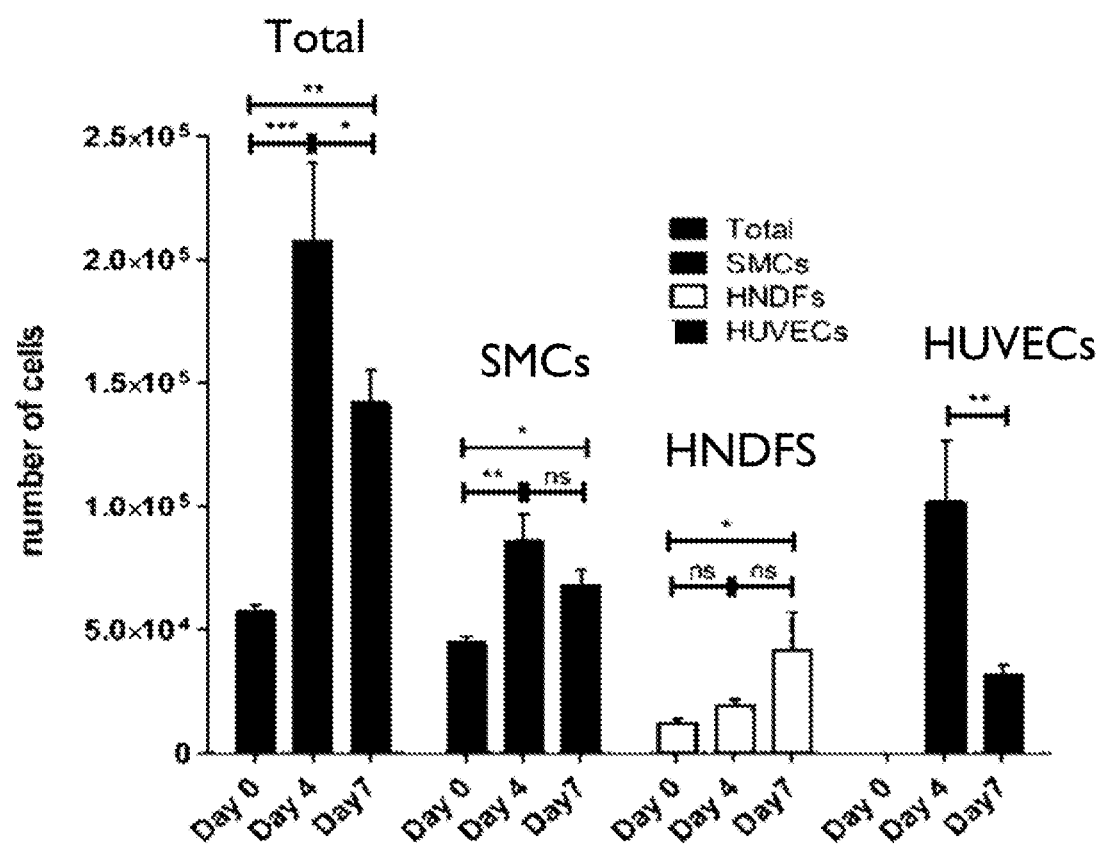
FIG. 8A depicts a bar graph showing layer-specific proliferation of the different cell types over the course of 7 days in the system analyzed via flow cytometric analysis, a p-value below 0.05 was considered statistically significant. HUVECs are human umbilical vein endothelial cells used for the tunica intima, SMCs are human vascular smooth muscle cells used for the tunica media, and HNDFs are human neonatal dermal fibroblasts used for the tunica adventitia.
Figure 8B:
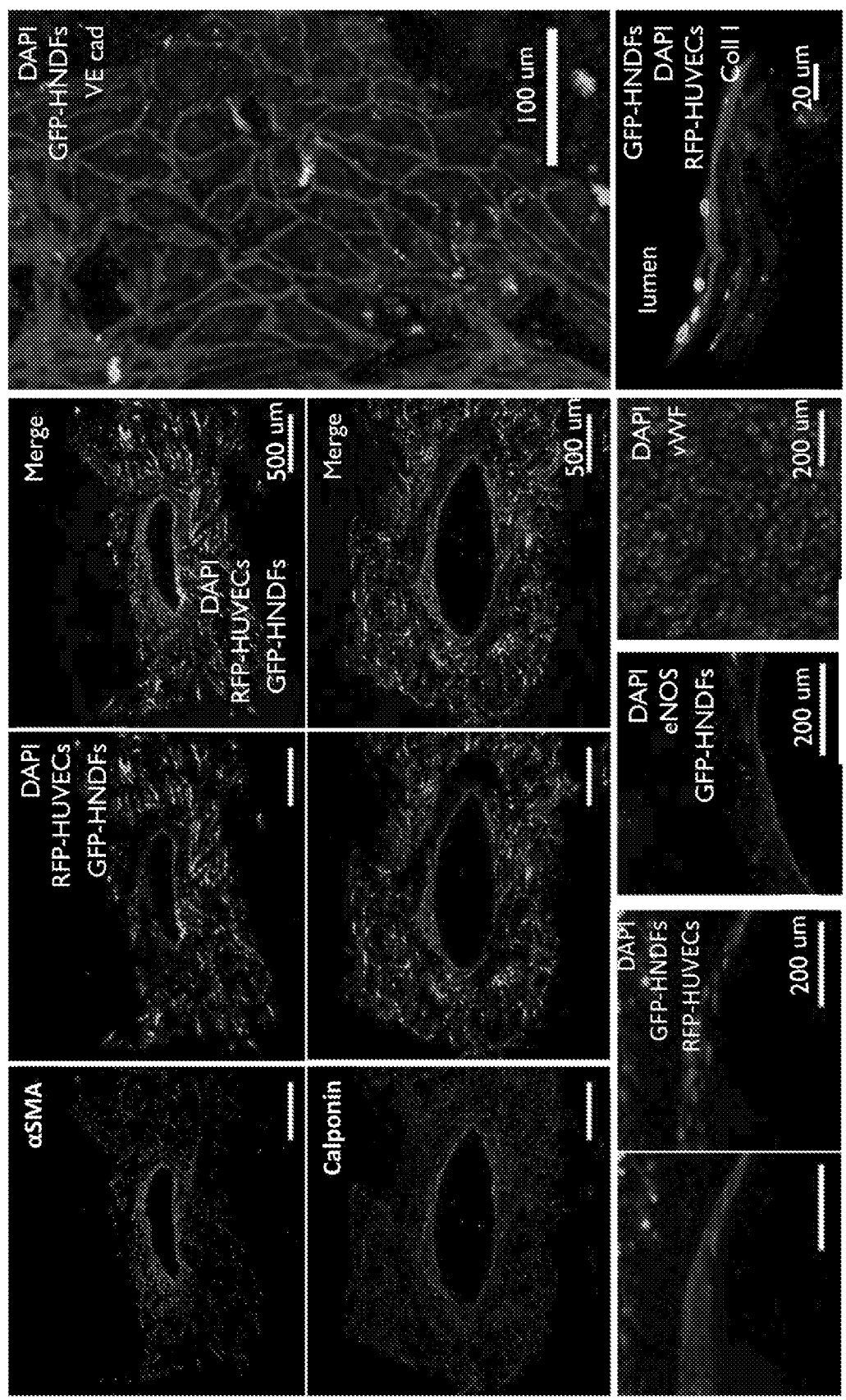
FIG. 8B depicts images showing marker expression of the various layers in the printed constructs after 2 weeks of maturation under active perfusion.
Figure 8C:
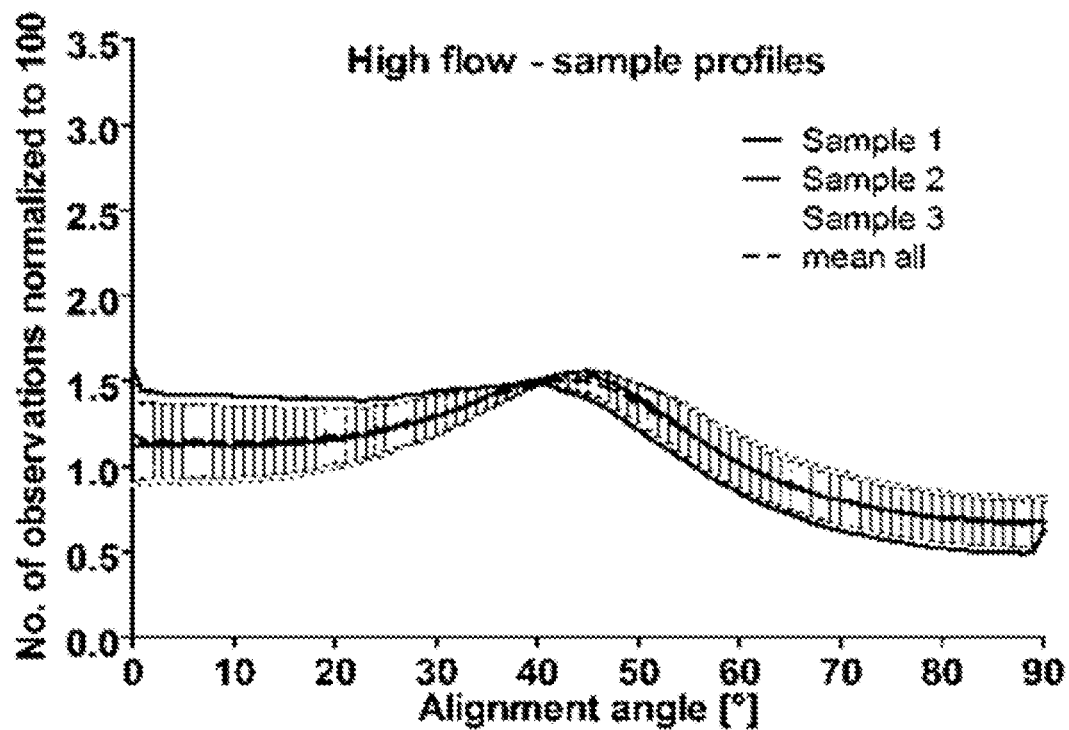
FIG. 8C depicts a graph showing alignment analysis of the subendothelial layer of cells. Alignment was analyzed via the OrientationJ Plugin in ImageJ and 6 different frames of upper or lower longitudinal section were analyzed per sample.

In certain embodiments, the multi-layered tubular construct is a branched multi-layered tubular construct. The branched multi-layered tubular construct may be created by employing two multicore-shell nozzles, one of which has an elongated core. Exemplary multicore shell nozzle designs were previously described in U.S. Provisional Patent Application Ser. No. 62/431,723, filed Dec. 8, 2016, entitled "Core-shell nozzle for three-dimensional printing and method of use," PCT Pub. No. WO 2018/106704; and PCT Pub. No. WO 2018/106705, which are hereby incorporated by reference in their entirety. FIGS. 8A through 8C illustrate exemplary multicore-shell nozzles.

In certain embodiments, the cell-laden filaments and/or the sacrificial filaments may include one or more functional chemical substances, such as drugs, small molecules, toxins, proteins, growth factors, and hormones.

The substrate for deposition typically comprises a material such as glass or other ceramics, PDMS, acrylic, polyurethane, polystyrene or other polymers. In some embodiments, the substrate may comprise living tissue or dehydrated tissue, or one of the extracellular matrix compositions described above. The substrate may be cleaned and surface treated prior to printing. For example, glass substrates may undergo a silane treatment to promote bonding of the cell-laden filaments to the glass substrate. In some embodiments, it is envisioned that the substrate may not be a solid-phase material but may instead be in the liquid or gel phase and may have carefully controlled rheological properties, as described, for example, in W. Wu et al., *Adv. Mater.* 23 (2011) H178-H183, which is hereby incorporated by reference. In the work of Wu et al., a fugitive ink was printed directly into synthetic hydrogels to create network structures. However, these synthetic materials do not support cell attachment and proliferation, limiting their use to non-biological applications. In the present disclosure, an extracellular matrix composition that facilitates cell attachment, migration, proliferation, and tissue-specific function while maintaining the appropriate rheology for printing is described. The multi-layered cell-laden and/or sacrificial filaments are embedded in the extracellular matrix composition during printing, and thus the at least partial surrounding of the tissue and sacrificial filament network with the extracellular matrix composition occurs during deposition of each of the multi-layered cell-laden and/or sacrificial filaments. This includes arbitrarily complex 3D structures that may require support material during printing. When the forming and embedding occurs simultaneously, as described above, the substrate onto which deposition occurs may be considered to be the container that holds the extracellular matrix composition or the extracellular matrix composition itself.

In certain embodiments, the substrate is plastic or glass.

In certain other embodiments, the substrate may be Matrigel. In certain other embodiments, as noted above, the substrate may be plasma treated or coated with a layer of at least one of Matrigel, poly L-lysine, geltrex, gelatin, fibrin, fibrinogen, fibronectin, nitogen, vitrogen, collagen I, collagen IV, chitosan, alginate, glycosaminoglycans, or any other biomaterial.

In certain embodiments, as described herein a substrate may be used to deposit the tissue construct components; in alternative embodiments, a substrate-free method incorporating embedded-printing may be used. Other methods of depositing a tissue construct in the housing are also contemplated (e.g., pin pull-out). Some alternative methods of printing three-dimensional living organs, producing organoids, embryoid bodies, endothelial sprouts, with or without embedded vasculature were previously described in PCT Pub. No. WO 2015/069619 and its corresponding U.S. Pat. Pub. No. US 2016-0287756 A1; and PCT Pub. No. WO 2016/179242, contents of which are incorporated by reference herein.

In certain additional embodiments, the method of producing a multi-layered constructs may also include a step of exposing the construct to one or more biological agents, a biological agent gradient, a pressure, and/or an oxygen tension gradient, thereby inducing angiogenesis of capillary vessels to and/or from the tissue construct. The one or more biological agents, the biological agent gradient, the pressure, and/or the oxygen tension gradient further direct development, differentiation, and/or functioning of the tissue construct. The "exposing" may be by flowing the one or more biological agents, like blood, growth factors or other cell types, like blood cells, through the core of the tubular, perfusable tissue construct or by intermittently stopping perfusion.

In certain alternative embodiments, the cell-laden multi-layered filament produced by the methods described herein may also include one or more coaxial and/or concentric fugitive ink layer(s) to produce one or more concentric tubule(s) that are not interconnected. For example, one multicore-shell filament can serve as a venous access while the other serves as an arterial access. Furthermore, in certain embodiments, there might be multiple arterial or venous access points represented by the multi-layered filament. Additionally, in certain embodiments, not all multi-layered filaments serve the function of a blood vessel, e.g., one filament could serve the function of a draining channel, similar in function to a ureter of collecting bile duct.

In certain other embodiments, the cell-laden multi-layered filament produced by the methods described herein may also include one or more coaxial and/or concentric layers that include growth factor(s), alone or in combination with one or more types of viable cells. Exemplary growth factors include fibroblasts growth factor, epithelial growth factor, vascular endothelial growth factor, insulin-like growth factor, platelet-derived growth factor, hormones like corticosteroids, or small molecules like blebbistatin.

In yet further embodiments, the cell-laden multi-layered filament produced by the methods described herein may include one or more coaxial and/or concentric layers that include materials that impart mechanical stability to the constructs. Such exemplary materials include polymeric materials like PLGA, PGA, PLA, PCL, polyurethane, polyhydroxyoctanoate or photocrosslinkable materials like GelMA, methacylated hyaluronic acid, or similarly modified biopolymers.

In yet alternative embodiments, the method may further include, prior to surrounding or encapsulating the tissue and/or network with the extracellular matrix composition, depositing one or more structural filaments layer by layer on the substrate in a predetermined pattern to form a mold. The structural filaments may comprise one or more structural materials selected from among the exemplary extracellular matrix compositions or extracellular matrix materials provided above. The mold may hold the extracellular matrix composition during the encapsulation and may remain as part of the tissue construct, or it may be removed after processing. The structural filaments may define the perimeter of the tissue construct on the substrate and all or at least a portion of the three-dimensional shape of the tissue construct out of the XY plane.

Certain embodiments relate to a method of producing a blood vessel construct, comprising depositing on a substrate one or more filaments, each filament comprising: a first cell-laden ink layer and a second cell-laden ink layer, the first and the second cell-laden layers being concentric and extending at least a portion of the length of the filament, the first cell-laden ink layer comprising a smooth-muscle cell (SMC)-containing cell-laden ink and the second cell-laden ink layer comprising a fibroblast-containing cell laden ink, and within the cell-laden ink layers a core comprising a fugitive ink, wherein the fugitive ink serves as a template for an open perfusable lumen within the filament; removing the fugitive ink to create the open perfusable lumen; after removing the fugitive ink, injecting a suspension of endothelial cells into the open perfusable lumen; and exposing the one or more filaments to fluid perfusion to induce cell proliferation and maturation thereby producing the blood vessel construct.

Multi-Layered Perfusable Tissue Constructs

Certain embodiments relate to a multi-layered perfusable tubular tissue construct produced by the described methods.

The tissue construct may have any desired 2D or 3D shape. For example, the tissue construct may have a planar geometry constructed from a single layer or multiple layers of multi-layered cell-laden filaments and an interpenetrating sacrificial filament network. Such structures may have any desired height (thickness). Typically, the tissue construct has a height of about 100 cm or less, about 10 cm or less, about 1 cm or less, about 1 mm or less, about 500 microns or less, or about 100 microns or less, and typically at least about 10 microns, at least about 100 microns, at least about 200 microns, or at least about 1 mm, with applications ranging from tissue cultures for implantation and drug screening to skin constructs and corneal replacements.

Alternatively, the tissue construct may have an arbitrary or application-dependent 3D size and shape. The tissue construct may have a solid structure, a porous structure, and/or a hollow structure (e.g., tubular or nontubular) and may be fabricated to mimic the morphology and function of particular organ. For example, the tissue construct may have the size and shape of a kidney, heart, pancreas, liver, bladder, vagina, urethra, trachea, esophagus, stomach, any segment of the intestinal tract, skin or other bodily organ. The 3D size and shape may in some cases be determined by a mold.

In certain embodiments, the tissue construct or part of a tissue construct may have a size and shape of hierarchical architectures similar to the human vasculature of arteries, arterioles, and small-scale vessels for, ultimately, implantation or suturing of a fully 3D printed tissue.

In certain embodiments, a printed multi-layered tubular construct produced by the described methods, comprises one or more filaments, each filament comprising: a plurality of concentric and coaxial cell-laden ink layers, each cell-laden ink layer comprising one or more predetermined cell types or clusters and extending at least a portion of the length of the filament, within the cell-laden ink layers an open perfusable lumen within the one or more filaments; a sacrificial filament network interpenetrating the one or more cell-laden filaments, each of the sacrificial filaments comprising a fugitive ink; and an extracellular matrix composition at least partially surrounding the one or more filaments and the sacrificial filament network. In addition, in certain embodiments, non-coaxial and concentric filaments containing one or more cell types, one or more types of cell clusters, or both may be printed into the construct.

In certain alternative embodiments, the cell-laden multi-layered filament(s) of the construct produced by the methods described herein may also include one or more coaxial and/or concentric fugitive ink layer(s) to produce one or more concentric tubule(s) that are or are not interconnected.

In certain other embodiments, the cell-laden multi-layered filament(s) of the tissue construct produced by the methods described herein may also include one or more coaxial and/or concentric layers that include growth factor(s), alone or in combination with one or more types of viable cells.

In yet further embodiments, the cell-laden multi-layered filament(s) of the tissue construct produced by the methods described herein may include one or more coaxial and/or concentric layers that include materials that impart stability to the constructs.

The printed multi-layered tubular construct may be a large scale vessel, an artery, an arteriole, a small-scale vessel, a vein, trachea, bronchus, airway tissue, milk duct, colon, lymphatic tissue, heart tube or intestinal section.

Uses

In certain embodiments, the methods described herein are for producing blood vessels.

In certain other embodiments, the methods described herein are for producing other tissues, such as bronchus, which may be implanted and function as such in the body. Other functional tissue structures may also be produced by the described methods, and include, e.g., ureter, trachea, esophagus, intestine, colon, lymph duct, milk duct, pancreatic duct, or bile duct, as well as nerve sheath.

In certain other embodiments, the multi-layered tubular tissue construct produced by the methods described herein can function as an interface with another printed tissue construct, fugitive network, or a body organ that enables a specific tissue function.

In certain other embodiments, the multi-layered tubular tissue construct produced by the described methods may be for suturing into a body or connecting a printed tissue construct adjacent to the multi-layered tubular tissue construct and in fluid communication with it to a desired host's circulation, like an implantation to a mouse's circulatory system or a human's circulatory system.

In certain other embodiments, the multi-layered tubular tissue construct produced by the described methods may be for maturation in vitro.

In certain other embodiments, the multi-layered tubular tissue construct produced by the described methods may be for use in vascular disease modeling.

In certain other embodiments, the multi-layered tubular tissue construct produced by the described methods may be for use in drug toxicity studies.

In certain other embodiments, the multi-layered tubular tissue construct produced by the described methods may be for use in drug screening applications.

In certain other embodiments, the multi-layered tubular tissue construct produced by the described methods may be for replacement of arteries, veins, arterioles, venules, etc. (regenerative medicine).

In certain other embodiments, the multi-layered tubular tissue construct produced by the described methods may be for replacement of tubular structures having concentric and coaxial cell layers within a body.

Disease Modelling

The described methods in reference to the biology of the printed blood vessel constructs opens interesting possibilities to study effects of inflammation and atherosclerosis in the blood vessel wall. The addition of acellular compounds (cholesterol crystals), bioactive molecules (tumor necrosis factor alpha) or additional cell types (macrophages/T cells/squamous cells) in the various layers of the printed construct could enable studying inflammatory processes and interventional therapies. Combinations with intra-vital imaging of the constructs and flowing of blood through the lumen could allow for studying thrombogenicity and adhesion of lymphoid/myeloid cells to the endothelium of the printed and matured construct. As a more biologically relevant tissue, studying in vivo phenomena could be enabled by this technology.

In certain embodiments, the tissue constructs produced by the methods described herein can be further developed into a disease model of varying vessel wall stiffness. A significant number of pathological processes, such as inflammation or fibrosis include stiffening of the vessel wall and hence inhibiting the body's ability to sustain a regulated blood pressure and flow profile. The stiffness of the printed hydrogel inks can be altered or chemical composition can be varied (like addition of collagen or hyaluronic acid) in order to study effects of extracellular matrix composition and mechanical properties on the maturation and performance of the printed vessel structure.

In certain embodiments, the printed cells or clusters of cells in the multilayered tissue construct might be diseased cells, like cancer cells or cancer cell aggregates, in addition to cells of cell clusters of the tissue of interest in which the cancer resides.

Seeding/Printing of Different Cells into the Putative Capillary Bed

As discussed herein, various form factors can be printed in both branching and hierarchical architectures. "Hierarchical architecture" encompasses the biological hierarchical organization of the vasculature tree from layer arteries and arterioles down the capillary beds supplying the organs/printed tissue with nutrients to then venules and larger veins. In certain embodiments, in the hierarchical printing method, the open capillary bed surrogate could incorporate additional printed or casted engineered tissue, such as, e.g., liver or pancreatic tissue, muscle tissue or kidney tissue.

Also, the structure of the printed capillary surrogate is not limited to the current design. In certain embodiments, it could be a 3D lattice structure or comprised of finer channels more hierarchically branched. The matrix around this bed could also be engineered to allow for angiogenesis and capillary sprouting from the main channel in order to perfuse the introduced tissue.

Taken together with the suturability and the separation between an arterial and a venous side access vessel, this entire platform could serve as a step closer to rapidly producing physiologically relevant engineered tissue that are entirely biocompatible and implantable (regenerative medicine applications).

Employing the Technique for Various Tissue Organizations

As the human body is partly as a network of tubes with open lumens, in certain further embodiments, this technology could be used to engineer different types of tissue other than the blood vessel, as described herein.

Other tissues in the human body are comprised of different cell types, but also have a concentric and coaxial layer structure. Since this nozzle design is meant for producing blood vessels, in preferred embodiments, it is designed for a trilayer printed structure.

In alternative embodiments, additional/more layers can be introduced to create, e.g., a 4- or 5-layer structure to incorporate more cell types. These layers could be designed to have all the same or varying thickness and could contain multiple cell types, clusters of cells and different ink formulations. For example, the intestinal wall is of high spatial organization of epithelial, muscular, and nervous tissue and built in this concentric and coaxial fashion. The perfusable lumen could serve as the intestinal lumen, the first layer could contain nervous and connective tissue cells, e.g., Meissner plexus neurons and fibroblast or clusters thereof, the second layer could contain intestinal smooth muscle cells or clusters thereof, the third layer could contain additional smooth muscle cells in a different orientation and nervous cells, e.g. Auerbach plexus neurons, and a fourth layer could contain connective tissue cells like fibroblasts. Another example is tissue of the larger airways, the bronchi are similarly constructed as the blood vessels with a contractile smooth muscle layer of a different cell type, specifically airway smooth muscle cells, and also have a connective tissue layer similar to the blood vessel adventitial layer surrounding the smooth muscle layer. In a bronchus-like printed multilayered tissue construct, in the first layer, there could be clusters of glandular cells dispersed in addition to the airway smooth muscle cells fulfilling the function of mucus production and secretion into the lumen. The open lumen in this case would be perfused with air not liquid. Other tubular structures, like the trachea or the esophagus are also constructed in a coaxial and concentric fashion, making this technique applicable more broadly. Advantageously, since the nozzle core and shell diameters can be arbitrarily changed, this system could be made fit to accommodate printing of those tissues with respect to their cell types and layer thicknesses.

As such, in certain embodiments, the methods described herein may be used to produce a multi-layered tissue construct, such as intestine, milk duct, sweat gland, colon, esophagus, stomach, airway epithelium, epididymis, urethra, liver bile duct, pancreatic duct, nephron, kidney, or lymph duct.

Apart from obvious iterations, altering cell types, material composition, or culture conditions of this system, one could imagine this technique to be applied to different tissues other than vasculature. Concentrically organized tissue structures like intestinal tissue, trachea, or bronchial and airway tissues could be manufactured in this printing method.

For the vascular application, improving biomimetic culture conditions could result in much stronger and more durable vessels, ultimately yielding a bioprinted construct of clinical relevance, not only on the implantation end, but also as a tool for modelling atherosclerosis, thrombotic events, or mechanisms of vascular inflammation. Scaling up the complexity of the construct by introducing e.g. macrophages into the layers to enhance tissue remodeling is easily done. Additionally, combination with other tissue engineering techniques renders this approach feasible for bringing tissue engineering towards actual implantable, physiologically relevant tissues for partial organ function replacement and disease modeling.

In alternative embodiments, the cell types functioning as the parenchyma could be pre-aggregated and dispersed in a layer of the multilayered construct with other cell types dispersed in the same layer alongside the aggregates. For example, primary isolated beta islets of the pancreas along with pre-aggregated or single cells of the exocrine portion of the pancreas derived from stem cells or primary isolation, could be printed into the first layer of the multilayered tissue construct. The second layer in this case could comprise endothelial cells and fibroblasts to form a vascular plexus to support the tissue. The perfused lumen in this case could be used to supply nutrients, but also as a site to sample the secreted enzymes, peptides, and hormones from the endocrine (beta islets) and exocrine part of the pancreatic cells present in the layers of the tissue construct.

Kits

Certain embodiments relate to kit. A kit may include the printed multi-layered tubular construct described herein along with hardware for chip assembly such as, for example, stainless steel bottom plates, acrylic lids, screws, printed gaskets, tubing components and perfusion pins; and instructional materials.

In certain embodiments, the kit may include parts to print the tissue. There, a kit may comprise: one or more cell culture media; a biomaterial or supporting material as mentioned above, for example, gelatin, fibrin, fibrinogen, transglutaminase, thrombin and gelatin methacrylate, collagen, glycosaminoglycans, collagen-acrylate (or a cross-linkable version) of any kind, Matrigel, poly lactic-co-glycolic acid (PLGA), alginate, and chitosan; one or more of the mentioned materials; or multiple cell sources, such as primary cells, embryonic stem cells, pluripotent stem cells, or cells differentiated from a stem cell type; cellular aggregates; growth factors and/or small molecules; custom designed nozzles or commercially available nozzles for extrusion-based bioprinting; hardware for chip assembly such as, for example, stainless steel bottom plates, acrylic lids, screws, printed gaskets, tubing components and perfusion pins; and instructional materials like a manual directing the recipient of the kit for proper use of the kit.

In certain embodiments, the described kits may also include analysis tools, such as a live/dead cellular staining protocol and the needed reagents, an assortment of staining reagents to stain the tissue of interest for common markers of that specific tissue (e.g. in the case of a blood vessel one or more adventitial markers, one or more medial markers, and one or more intimal markers); histological staining components to visualize tissue damage or matrix remodeling; primers and other reagents for PCR applications, such as polymerases (e.g., to investigate expression levels of common markers or disease markers for the tissue of interest).

EXAMPLES

Example 1: Printing Robust Human Vasculature Via Multicore-Shell 3D Printing

Materials and Matrix Formulations
1. Biomaterial Preparation and Ink Formulations The protocols for preparation of cell-laden and fugitive inks were adopted from Kolesky et al. (Kolesky et al., *Adv Mater.* 2014; 26(19):3124-3130; Kolesky et al., *Proc Natl Acad Sci USA.* 2016; 113(12):3179-3184). Cell-laden inks were used to print the medial and adventitial layers of the printed vessel as inner and outer shell, respectively, whilst the fugitive inks served as template for the open perfusable lumen. Once the construct was stably encapsulated, the fugitive ink was removed and an open channel was perfused.

2. Preparation of Reagents

Gelatin from porcine skin was dissolved at 15 w/v % in phosphate-buffered saline (PBS) without calcium or magnesium while stirring at 70° C. The solution was processed at 70° C. for 12 h, the solution's pH was adjusted to 7.5 by titration with 2 N sodium hydroxide, and filtered warm using a sterile 200 nm pore size standard cell culture filter. All solutions were stored in solid-state aliquots at 4° C.

For ink formulation, the aliquots were melted to liquid state in a 37° C. warming block. Fibrinogen was prepared freshly each print session. It was dissolved at 80 mg/mL and left undisturbed for at least 30 min in PBS without calcium or magnesium to avoid precipitation. Pluronic F127 was homogenized with a speed mixer at 40 wt. % in sterile deionized water, and stored at 4° C. From this stock, the fugitive ink was made.

Thrombin from bovine plasma was dissolved in sterile deionized water at 2000 U/mL and stored in aliquots at −20° C. Calcium chloride was dissolved at 250 mM as a stock solution and sterile filtered. Transglutaminase (Moo Gloo) was prepared freshly for every print session: It was dissolved at 6 w/v % in PBS without calcium or magnesium for 30 min at 37° C. and sterile filtered once dissolved. 22
3. Cell-Laden Ink Preparation For the smooth muscle cell (SMC)-containing ink and the fibroblast (GFP-HNDF)-containing cell-laden inks, respectively, the formulation of the ink was 7.5 w/v % gelatin, 20 mg/mL fibrinogen, and 2.5 mM calcium chloride in PBS without calcium or magnesium unless otherwise indicated. The fibroblasts were dispersed in PBS before mixing into the ink at 0.5 million cells/mL (final concentration). SMC ink was brought to 8-10 million cells/mL depending on availability of cells. All inks were mixed well at 37° C. by gentle pipetting to ensure proper resuspension of the cells in the viscous ink. Cell-laden inks were loaded into syringes and cooled to 4° C. for 15 min to induce thermal gelation of the gelatin. Before printing, the inks were equilibrated to room temperature for 15 min.
4. Fugitive Ink Preparation The fugitive ink was prepared from the 40 wt % Pluronic mixture. It was diluted to 33 wt % and thrombin was added at 50 U/mL to induce rapid polymerization of the fibrinogen in the cell-laden inks upon printing. The ink was homogenized by speed mixing, loaded into a dispensing syringe, cooled to 4° C. and centrifuged to remove air bubbles. Before printing, the fugitive ink was equilibrated to room temperature for 15 min to solidify it and make it suitable for printing.
5. Cell Culture SMCs, GFP-HNDFs, and RFP-labeled human umbilical vein endothelial cells (RFP-HUVECs) were cultured as according to their respective manufacturer's protocol, and not used in experiments past passage 10, 15, and 12, respectively. When used in a print session, the cells were trypsinized for collection and subsequent ink preparation. All cell types were counted via an automated cell counter (Cellometer) according to manufacturer's protocols and diluted to the target number of cells to add to the cell-laden inks. To concentrate the cells, they were centrifuged at 220 g and the supernatant was aspirated. The cells were resuspended in the PBS compartment of the ink formulation and mixed with gelatin, fibrinogen, and calcium chloride as described in the paragraph above.
Printing Technique
1. Printer Details The 3D printer used for all the experiments was a custom-built Aerotech 3D Printer with an overall size of 725 mm×650 mm×150 mm. Four print heads with a syringe barrel or nozzle attached were individually addressed and controlled. A mounted camera was used to define X, Y, and Z coordinates of the nozzle in respect to the printing substrate, and to determine X and Y offsets between the two nozzles on the different print-heads for multi-material 3D printing.

For blood vessel printing, a syringe containing the fugitive ink with a 0.4 mm inner diameter straight metal nozzle (EFD Nordson) was mounted in the syringe barrel of the first printhead. The multi-core shell nozzle was attached to the second printhead via a small adapter plate and the syringes with the respective cell-laden inks were mounted on top of the nozzle. Room temperature is kept at 20° C.-21° C., below the reverse gelation point of the gelatin inks. If the room is reaching too high of a temperature, a cooling system can be attached to the cell-laden ink syringes to maintain ink temperature of 20° C. In order to facilitate stable printing on soft and slippery hydrogels, the multicore-shell nozzle was tilted 45° to the right to enable printing of the 3-layer filament close to the substrate. All syringes were connected to individually controlled compressed air driven pressure boxes (EFD, Nordson) to extrude the respective ink upon printing. The printer was controlled by a custom written G code program for this particular application loaded and edited in the printer software (Aerotech CNC Operator Interface/Aerobasic Editor).
2. Nozzle Printing The multicore-shell nozzle design was used as described in U.S. Provisional Patent Application Ser. No. 62/431,723, filed Dec. 8, 2016, entitled "Core-shell nozzle for three-dimensional printing and method of use," incorporated by reference in its entirety. It is a tapered tri-layer nozzle with coaxially and concentrically organized shells. The generated part was printed on a stereolithography printer (Aureus, EnvisionTec) with a resin crosslinking at 700 W/dm2 (EnvisionTec). After printing the nozzle was carefully detached from the building platform, rinsed with isopropanol and water, and air-dried. The printed nozzles were good for 3-4 print sessions, after that clogging issue with the nozzles occur.
3. Gasket Printing The gaskets that house the subsequently printed constructs were printed in a two-component silicone elastomer (SE 1700) on a 75×50 mm glass slide. Base and platinum-based crosslinker for the two-component system were mixed 10:1 by weight using a Thinky at a speed of 2000 for 5 min. Using a previously published Matlab script for G code generation (Kolesky et al., *Proc Natl Acad Sci USA*. 2016; 113(12):3179-3184), the gaskets were designed to hold a 4.5 cm long printed vessel, suspended in matrix. The inlets the perfusion pins (1.27 mm outer diameter) were 5.2 mm above the bottom of the glass slide. To securely position the perfusion pin and ensure a tight fit between pins and gasket to avoid leakage, the diameter of the opening in the PDMS gasket was 0.4 mm, about a third the outer diameter of the perfusion pin. PDMS is stretchable and can close tightly around the pin. Overall height of the printed gasket was 8.8 mm, rendering the total volume of the gasket to ~6 mL.

For printing, the elastomer was prepared with the catalyst in a ratio of 10:1 by weight and loaded into a syringe and centrifuged for 5 min at 3000 g to remove air bubbles. Via a Luer lock connection, a tapered plastic nozzle with an inner diameter of 410 μm (EFD Nordson) was connected to the syringe and zeroed on the print substrate. The gasket was printed onto the glass slide from the aforementioned G code and cured overnight at 80° C. in a furnace.
4. Construct Fabrication Process The printed vessel construct fabrication process was adopted from Kolesky et al. (Kolesky et al., *Proc Natl Acad Sci USA*. 2016; 113(12):3179-3184), and this protocol was altered to incorporate the multicore-shell printing (see, e.g., PCT Pub. No. WO 2016/019087). Following the bioprinting process, the construct was completed by casting a top hydrogel matrix to encapsulate the printed features. Subsequently, the fabricated construct was assembled into a perfusion system, allowing for flow of cell culture medium through the open lumen. All components for assembling the perfusion chips were autoclaved apart from the peristaltic tubing, which had to be ethanol sterilized. The construct can be subdivided into bottom, printed vessel, and top matrix.

Two processes to produce the bottom part of the construct were used, one where the printing was done on fully crosslinked dried bottom layer, and one where printing was performed on thermally gelled hydrogel bottoms.

For the dried hydrogel variant, the matrix was comprised of 7.5 w/v % gelatin, 10 mg/mL fibrinogen, 2.5 mM calcium chloride, and 0.2 w/v % transglutaminase in PBS without calcium or magnesium. The liquid mixture was incubated for 15 min at 37° C. to pre-crosslink the matrix with the transglutaminase.

Following incubation, 1 mL of the bottom matrix was mixed with 1 U/mL thrombin to induce rapid transformation of fibrinogen to fibrin and quickly cast into the gasket making sure that the glass was completely covered. After the fibrin was completely formed, the bottom matrix was air-dried for 1.5 h on a 37° C. heating plate. Perfusion pins were pushed through the inlet in the gasket (0.84 mm inner diameter) and into these pins; smaller pins (0.82 mm outer diameter) were placed to make sure no matrix enters the pins upon casting in the final step. If these inner pins were left out, the perfusion pins would be open during casting of the top matrix, and the liquid matrix could enter the perfusion pin leaving the lumen blocked. The inner pin was sticking out about 1 mm out of the outer perfusion pin to facilitate optimal connection of the fugitive ink with the inner pin to produce a continuously perfusable construct. Inner pins were pulled out after casting. The pin location was the (x,y)=(0,0) coordinate of the printer and the (z)=(0) coordinate of all nozzles was the substrate surface. A pillar of fugitive ink was printed onto the dried bottom to facilitate connection to the printed vessel. Subsequently, the vessel was printed by first connecting the fugitive ink core to the printed pillar and then starting to extrude first the SMC ink to form the inner shell around the fugitive ink. Right after switching on extrusion of the SMC ink, the GFP-HNDF cell-laden ink was switched on to add the outer shell of the printed vessel. Upon reaching a length of 45 mm for the multicore-shell printed filament, the cell-laden inks were switched off and the fugitive ink, still extruding, was used to connect to the perfusion pin on the other side of the gasket. After printing was finished, the gasket was carefully filled in with the top matrix. The top matrix was prepared in the same fashion as the bottom matrix (see above) and 4.5 mL were mixed with 1 U/mL thrombin before casting, again to induce rapid transition of fibrinogen and proper connection between bottom matrix, printed construct and top matrix. Full crosslinking of the construct was achieved via the slow-acting transglutaminase in a later incubation step. For printing on thermally gelled hydrogels, the first layer of the bottom gel was prepared and casted exactly as in the dried hydrogel variant. The bottom layer was not dried but equilibrated to room temperature, and a 1 mL layer of 7.5 w/v % gelatin, 10 mg/mL fibrinogen, and 2.5 mM calcium chloride in PBS was cast on top of the already crosslinked hydrogel layer. The second layer was covered with a glass slide to reduce water evaporation and thermally gelled for ~30 min at room temperature. Subsequently, it was subjected to the same printing process as described above. During method development, prints were initially cell-free, and the different layers were labeled with FITC-conjugated gelatin or rhodamine-conjugated fibrinogen (Kolesky et al., *Proc Natl Acad Sci USA*. 2016; 113(12):3179-3184) or aqueous fluorescent Risk Reaktor dyes at a dilution of 1:1000 (FIG. 8E).

5. Hierarchical and Branched Printing

For hierarchical and branched printing the hydrogel inks were prepared cell-free for initial testing of the code. For branched printing an additional multicore-shell nozzle with an elongated core part was used to penetrate the already trilayer filament and connect the fugitive ink cores. Printing of the branched constructs was performed in a gasket with two inlets and two outlets, where only one inlet was supplied with a perfusion pin. The printed branched construct was encapsulated in hydrogel ink and the fugitive ink was evacuated to test perfusion of both branches.

Hierarchical printing was enabled by using another nozzle depositing fugitive ink, penetrating the already printed trilayer filament in the same way as the multicore-shell nozzle with an elongated core. To print a surrogate capillary bed for demonstration purpose, the fugitive ink in the hierarchical printing was connected to the core of an already printed trilayer filament on the top and then a branching capillary network was printed directly onto the hydrogel. For connection with the lower already printed trilayer filament, the fugitive ink was brought down into the core ink part of the already printed filament, piercing the outer vessel layers and the construct was subsequently encapsulated in hydrogel matrix. After evacuation of the fugitive ink, the construct was perfused with a red dye to test for full connection of the structures.

Figure 5:
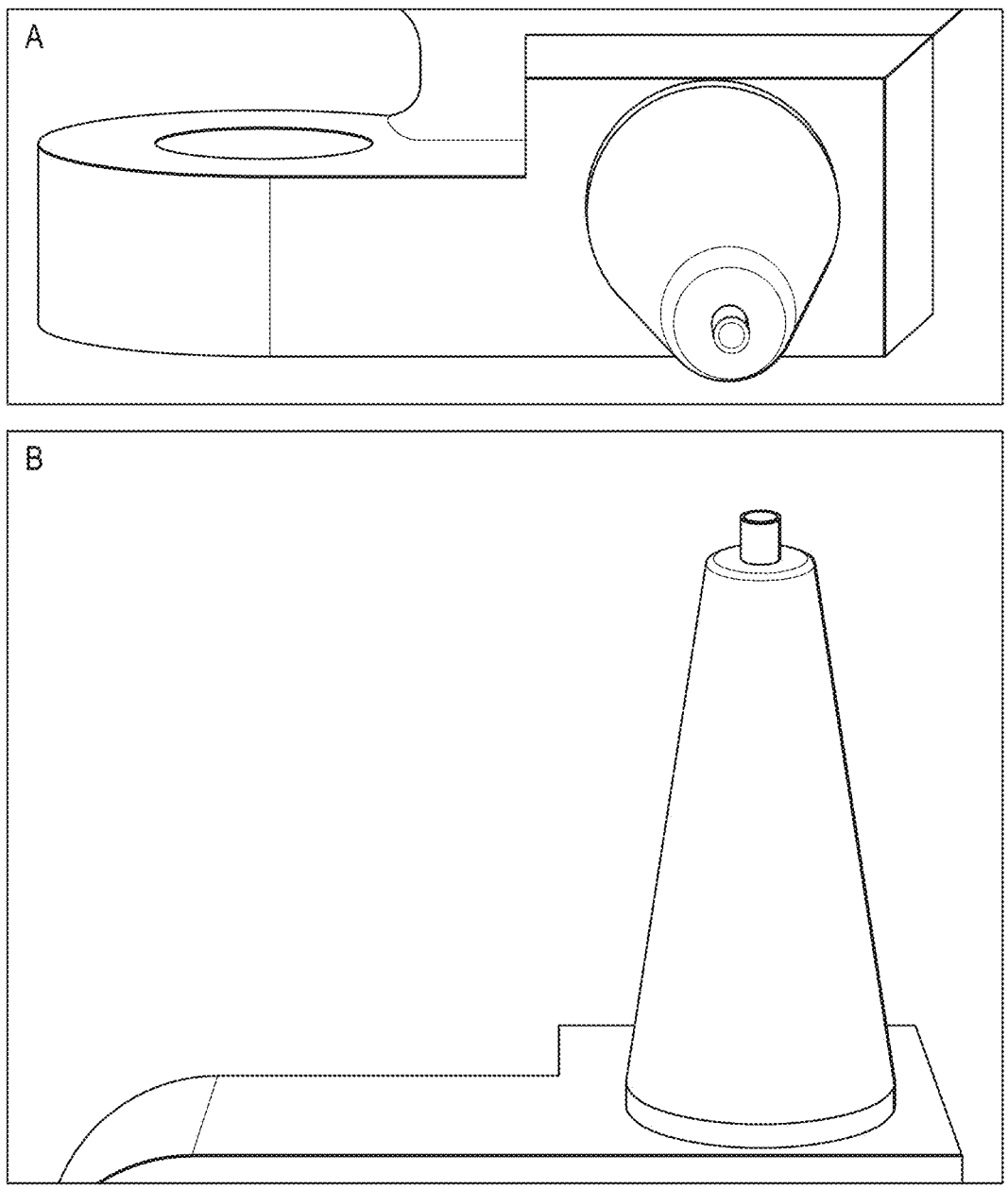
FIG. 5 illustrates the described herein printing technique and materials: (A) shows the bottom view of the multicore-shell nozzle; (B) shows a multicore-shell nozzle with an elongated core nozzle; (C) shows a side view of the multicore-shell filament printed onto a hydrogel substrate; (D) shows the multicore-shell filament encapsulated in matrix and set in its perfusion system housing; and (E) shows the chip cross-section schematic.
Figure 5:
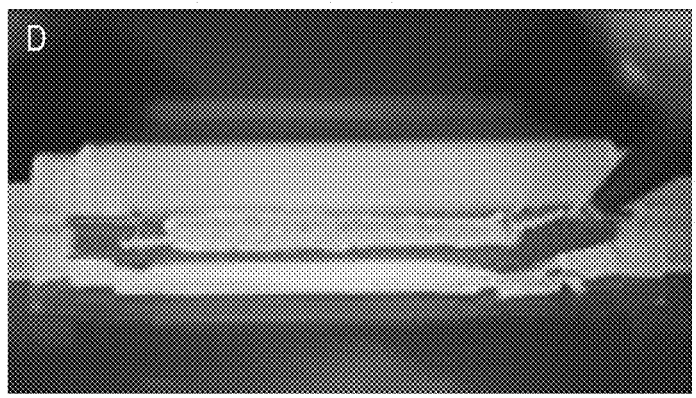
Figure 5:
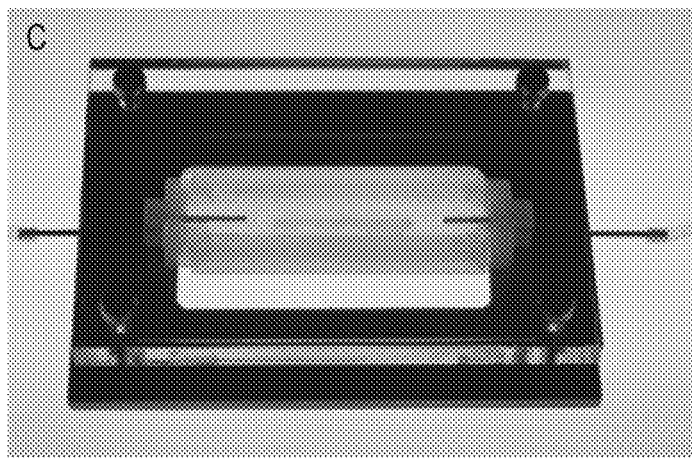
Figure 5:
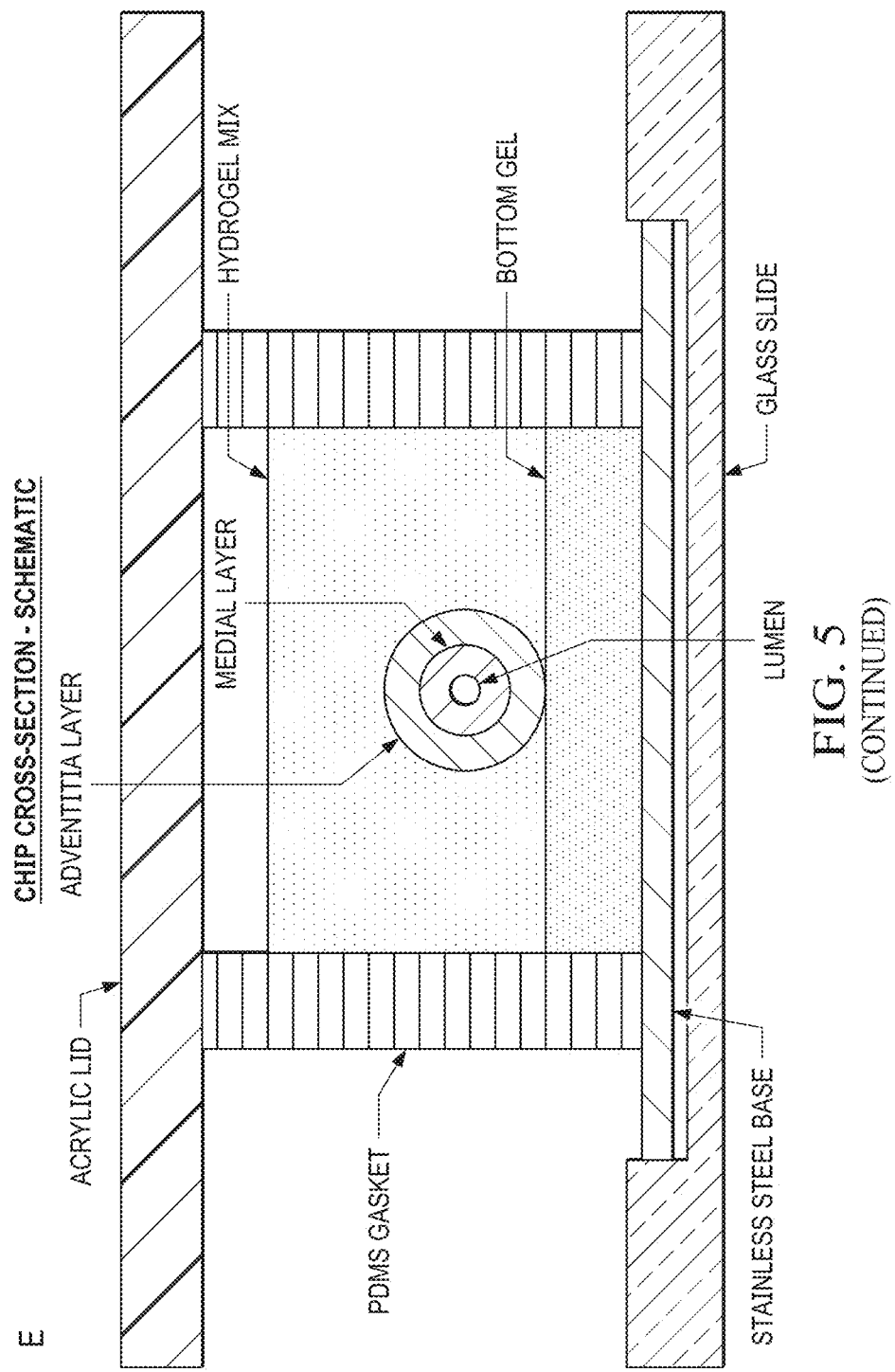
Figure 14A:
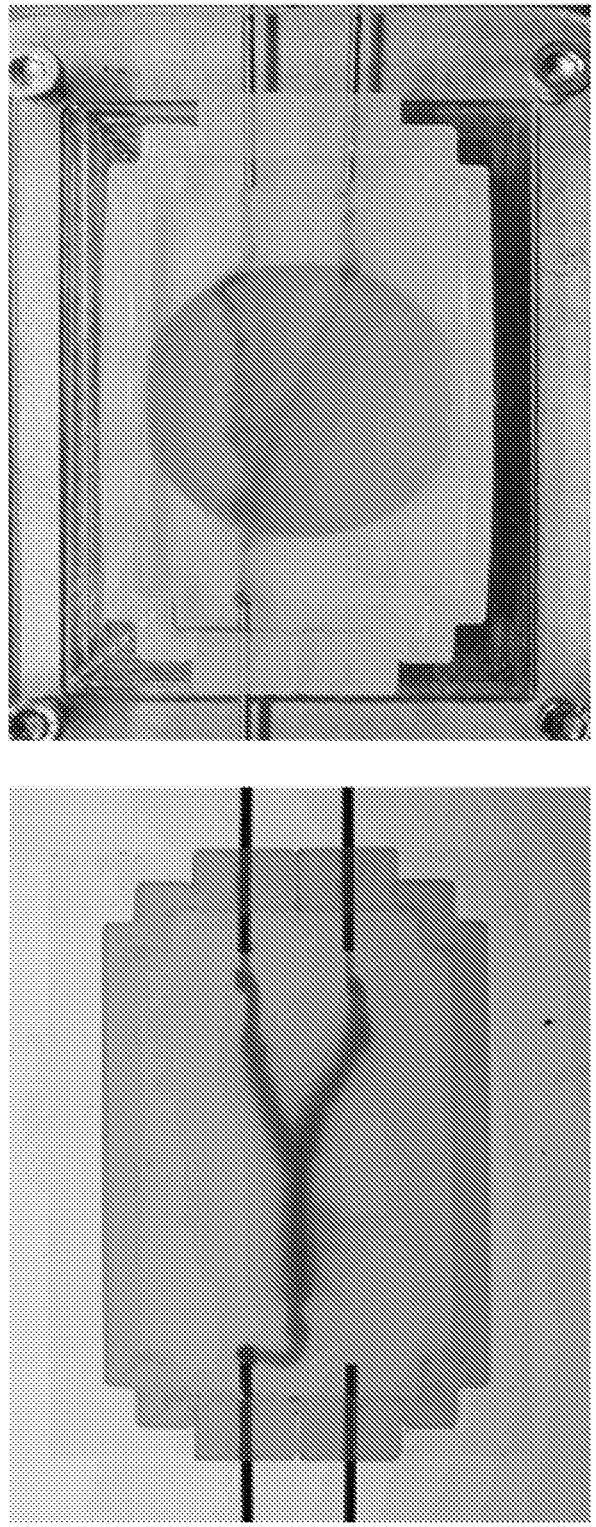
FIG. 14A depicts images of branched prints perfused with a red dye of equal branching (left) and a higher order and lower order branch (right).
Figure 14B:
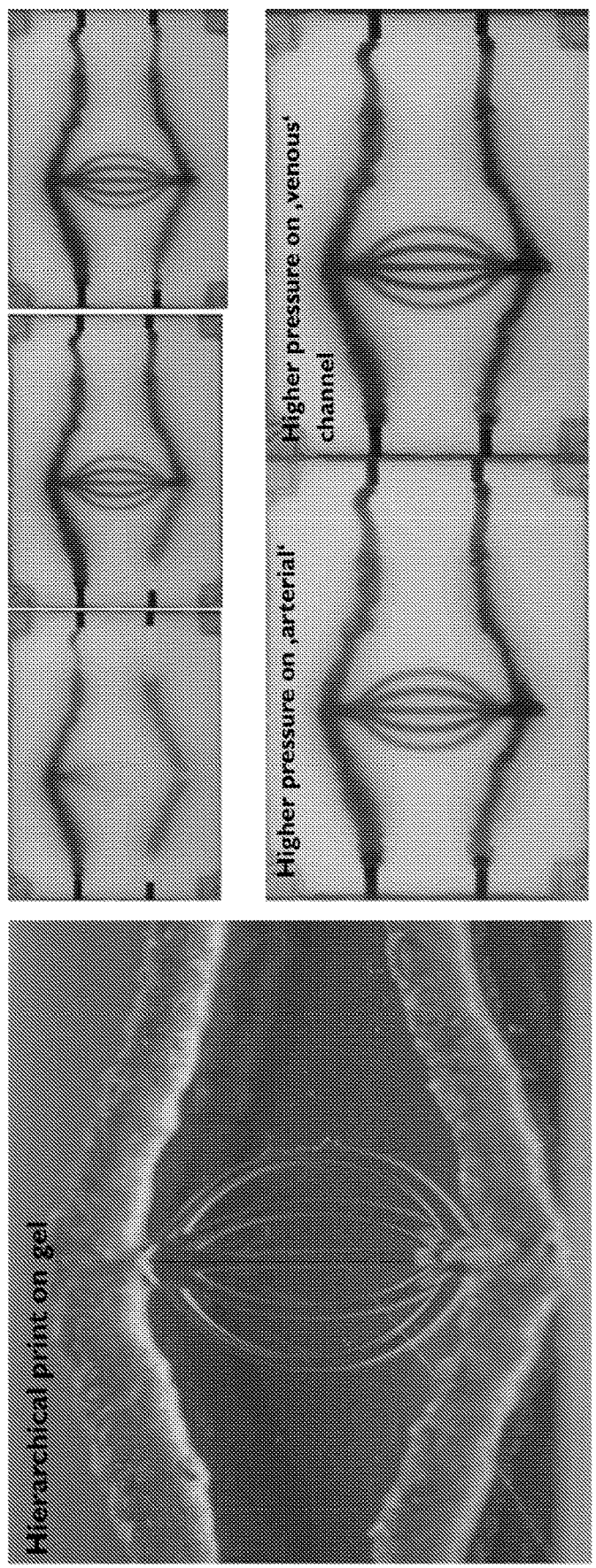
FIG. 14B depicts images of hierarchical printed structures with two main 'vessels' and a capillary bed surrogate (transparent ink, left). The structure was encapsulated and perfused (right series) with a red and a blue dye to visualize an 'arterial' and a 'venous' side access for the printed construct.

FIG. 14 illustrates examples of branched and hierarchical printing. For branched printing the core part of the nozzle is elongated (FIGS. 5A and 5B). For hierarchical printing, the ink employed for the interconnecting structure is the core ink without the surrounding layers.

Branched and hierarchical prints enable interfaces with other biologically active tissue under continuous perfusion.

6. Post-Processing and Perfusion

After casting the top matrix, the matrix was gelled at room temperature for 5 min and subsequently transferred to a 37° C. incubator for 2 h to fully crosslink the structures via the slow-acting transglutaminase. Following incubation, the construct was cooled to 4° C. for 15 min to thermally stabilize the gelatin-containing matrix and liquefy the fugitive ink comprised of Pluronic. In a sterile environment, the perfusion chip was assembled as previously described: the inner pins were pulled from the perfusion pins and tubing was attached to outer ends of the pins. At the inlet of the construct, a syringe reservoir (EFD Nordson) was attached containing 10 mL of incubator equilibrated SMC cell culture medium (5% CO2 environment at 37° C.) supplemented with additional 1% antibiotic, antimycotic solution and 8% fetal bovine serum (FBS). A 0.2 μm sterile filter was attached via a Luer lock connection to the outlet of the syringe. A nozzle matching the inner diameter of the peristaltic tubing (PharMed BPT) was connected to the outlet of the filter, and the peristaltic tubing was used to connect medium reservoir and perfusion pin at the inlet of the chip. Cell culture medium was used to flush out the now liquid fugitive ink. After sufficient washes of at least three times the open channel volume, the systems' circulation was closed with silicone tubing attached to the outlet perfusion pin that returned the perfusate back into the syringe reservoir via a small connector pin in its lid. The entire perfusion system was connected to a peristaltic pump (Ismatec) located in a 37° C., 5% CO2, and 95% humidity cell culture incubator. Perfusion rate was set to 100 µL/min up to 2 mL/min, unless otherwise stated, and the construct was continuously perfused. Cell culture medium was changed every other day. As additional controls, small leftover amounts of the cell-laden inks were encapsulated into the top matrix by extruding the cell-laden ink into a 12-well cell culture plate and casting 0.5 mL of top matrix mixed with 1 U/mL thrombin over it. These samples were subjected to the same cell culture medium conditions as the perfused samples as well.

Calculated shear stresses for vessel diameters from 0.8 mm-1 mm:

100 µL/min 0.2586 dyn/cm$^2$-0.1324 dyn/cm$^2$ 0.2 cm/s-0.5 cm/s

600 µL/min 1.5518 dyn/cm$^2$-0.7945 dyn/cm$^2$ 1.7 cm/s-1.9 cm/s 2.23 mL/min 2.9529 dyn/cm$^2$-5.7674 dyn/cm$^2$ 4.7 cm/s-7.4 cm/s Endothelial Cell Seeding On day 1 after printing (early endothelialization) or 3 to 4 days after printing and construct perfusion (late endothelialization), the inside of the vessel construct was seeded with endothelial cells (RFP-HUVECs or Tert2 immortalized HUVECs). Endothelial cells were trypsinized and collected at a concentration of 5-7.5 million cells/mL. Perfusion was stopped and the constructs were transferred into a sterile environment. Cell culture medium in the reservoir was aspirated and replaced by endothelial cell culture medium with 1% antibiotic and antimycotic solution (Anti/anti) and 8% FBS added, unless otherwise indicated. There, the outlet silicone tubing was cut, leaving a small piece still attached to the metal outlet pin. A pipet containing 150 µL of cell suspension was attached to the outlet and the cell suspension was slowly pipetted into the channel. Pipet tip and tubing was removed, and outlet silicone tubing was re-attached. The entire construct was transferred to the incubator and circulation of medium was interrupted with two tubing clips closing inlet and outlet, respectively, to ensure the cells remain in the channel. After 30 min, the construct was flipped upside-down to make sure the channel was evenly exposed to endothelial cells. The construct was left at 37° C. without perfusion overnight or for more than 7 hours and put back into perfusion the next day.

Special Interventions

In order to determine vessel wall morphology under different media conditions, constructs were printed and seeded normally at day 4. For 'low serum conditions,' serum addition was progressively reduced with every medium change (every other day), from 8% to 5% to 3% to zero. For 'medium serum conditions,' FBS was constant at 8% throughout the experiment. Effects of different flow rates were examined using two different types of peristaltic tubing (yielding 100 µL/min vs 600 µL/min of cell culture medium for 'low' and 'medium' flow conditions). Investigations involving addition of a focal adhesion kinase inhibitor (PF 573228, 200 nM) to inhibit integrin signaling, withdrawal of antibiotics to remove stretch-activated-ion-channel-blockers, or 'high' flow conditions (2.23 mL/min vs 100 µL/min) were performed with constructs printed and seeded in the same manner as described above. One day after endothelial seeding, the aforementioned culture medium conditions were started. Medium was changed every other day and the samples were fixed on day 14 after printing.

Analysis Techniques

1. Live/Dead Staining and Analysis

Live/dead cell staining with ethidium homodimer and calcein to investigate cell viability during the printing process and after 1 week of perfusion was performed using a kit containing the two dyes (Live/dead stain, Molecular Probes) according to the manufacturer's instruction. First and last prints of a print session were incubated in the staining solution and imaged on a confocal microscope right away to investigate longevity of the cells in the inks and viability after extrusion through the nozzle where the cells experience high shear. Cast controls and samples from 1 week of perfusion were also stained and imaged. Six fields of view per sample and one sample per print condition and cast control condition were analyzed. Cell counting was performed using a custom-written FIJI macro for batch analysis utilizing the 3D Objects Counter feature of the program (Kolesky et al., *Adv Mater.* 2014; 26(19):3124-3130), and the resulting data were processed in GraphPad Prism.

FIG. 6A shows a representative cell viability confocal microscopy image of live and dead cells stained with a mammalian cell live/dead staining kit (calcein AM and ethidium bromide homodimer). FIG. 6B shows a bar graph of the live/dead cell data obtained from analysis of confocal images (n=6). First and last print were analysed to determine viability during the printing process.

FIG. 6A shows great cell viability in the first print.

As shown in FIG. 6B, variation in cell viability in different conditions was not significant.

2. Immuno-Fluorescent Staining

At the end of an experiment, the samples were fixed in formalin if not otherwise indicated. The perfused constructs were taken out of the incubator and first washed with 5 mL PBS containing calcium and magnesium by gravity feed with a pressure head of 40 cm (~4 kPa). Subsequently, formalin was flushed into the chip and the inside of the channel was fixed for 15 min at room temperature. The chip was taken apart and the perfusion pins were pulled out of the construct. The hydrogel construct was taken out of the gasket and transferred to a 15 mL conical tube containing 9 mL formalin to complete the fixation process with an additional 45 min of fixation. Slice cultures and cast controls were washed in PBS for 5 min and subsequently fixed for 30 min at room temperature in formalin. Fixed samples were washed two times in PBS and either stored at 4° C. in PBS with 0.01% Triton X-100 or directly subjected to immuno-fluorescent staining. For immuno-fluorescent staining, samples were permeabilized with 0.25% Triton X-100 in PBS for 30 min and blocked in 5% donkey serum for 1 day at 4° C. Primary antibodies (see list) were incubated in the respective dilutions in PBS with 0.1% Triton X-100 and 0.5% bovine serum albumin (BSA) for 2 days at 4° C. Afterwards, samples were washed 3 times for 3 h on a shaker at room temperature. Secondary antibody or fluorophore-conjugated phalloidin incubation for 8 h at room temperature in the respective dilution and species-specific combinations was performed after washing the samples. DAPI (1 µg/mL) was added during the last 2 h of the secondary antibody step and the samples were afterwards again washed 3 times for 3 h each. Samples were imaged at a ZEISS upright laser scanning confocal microscope (LSM710). 3D reconstruction of selected images was conducted using Imaris 7.6.4, Bitplane Scientific Software. 30

Figure 8D:
FIG. 8D shows a still 3D reconstruction image of capillaries invading the vessel wall.

FIG. 8A depicts layer-specific proliferation of the different cell types over the course of 7 days in the system analyzed via flow cytometric analysis, a p-value below 0.05 was considered statistically significant. FIG. 8B shows marker expression of the various layers in the printed constructs after 2 weeks of maturation under active perfusion. FIG. 8C shows alignment analysis of the subendothelial layer of cells. Alignment was analyzed via the OrientationJ Plugin in ImageJ and 6 different frames of upper or lower longitudinal section were analyzed per sample. FIG. 8D shows a still 3D reconstruction image of capillaries invading the vessel wall.

Figure 9:
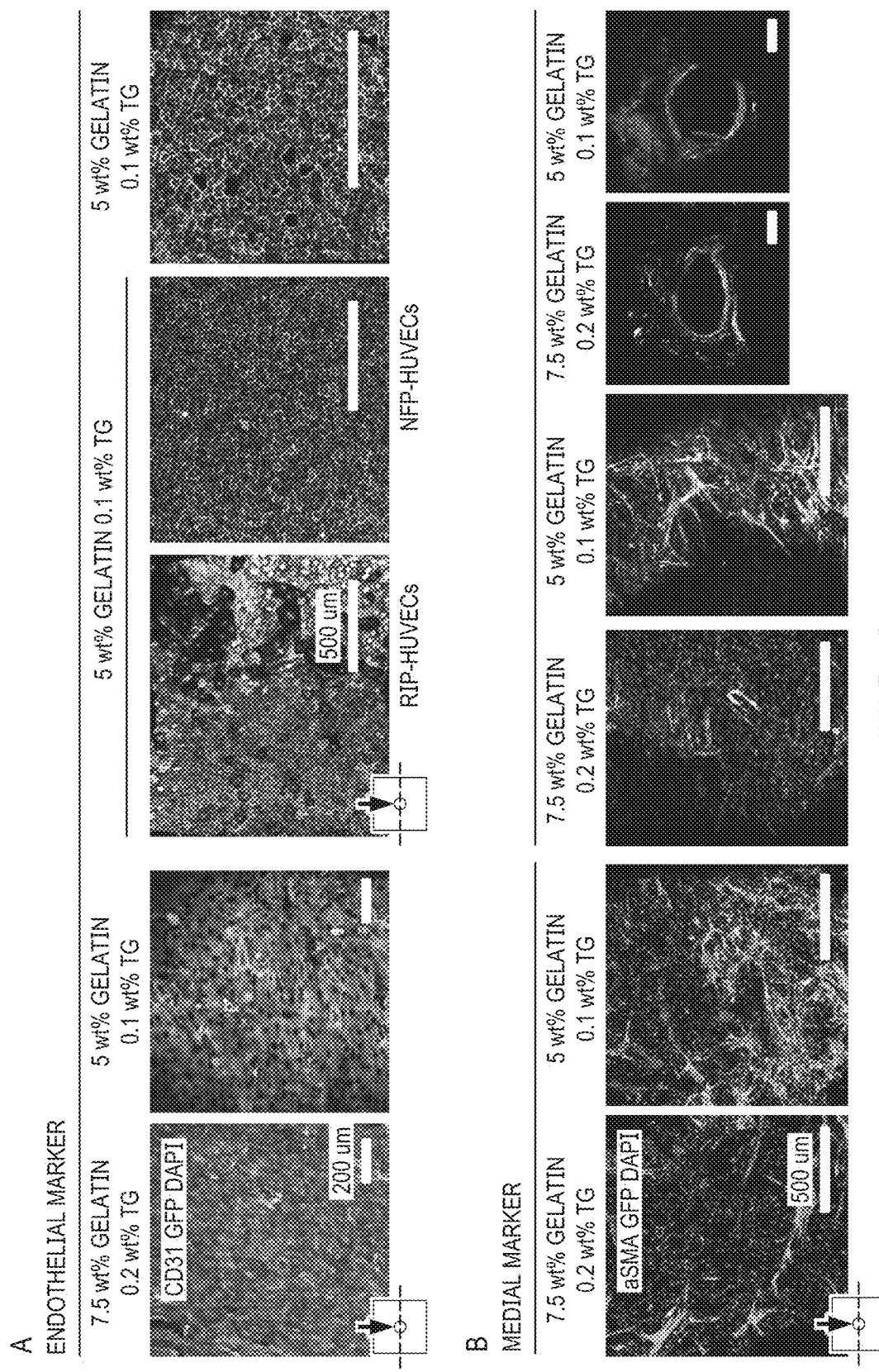
FIG. 9 depicts: (A) Confocal images of longitudinal cross-sections for endothelial marker expression in construct matured for 4 weeks in two different extracellular matrix compositions with (left panels) or without (right panels) fully printed wall structures. RFP-HUVECs do not perform as well and can be replaced with 'normal' HUVEC cells not expressing a fluorescent marker; and (B) Confocal images of longitudinal and horizontal cross-sections for medial marker expression in construct matured for 4 weeks in two different extracellular matrix compositions. Smooth muscle cells express specific markers for up to 4 weeks of culture time.
Figure 10:
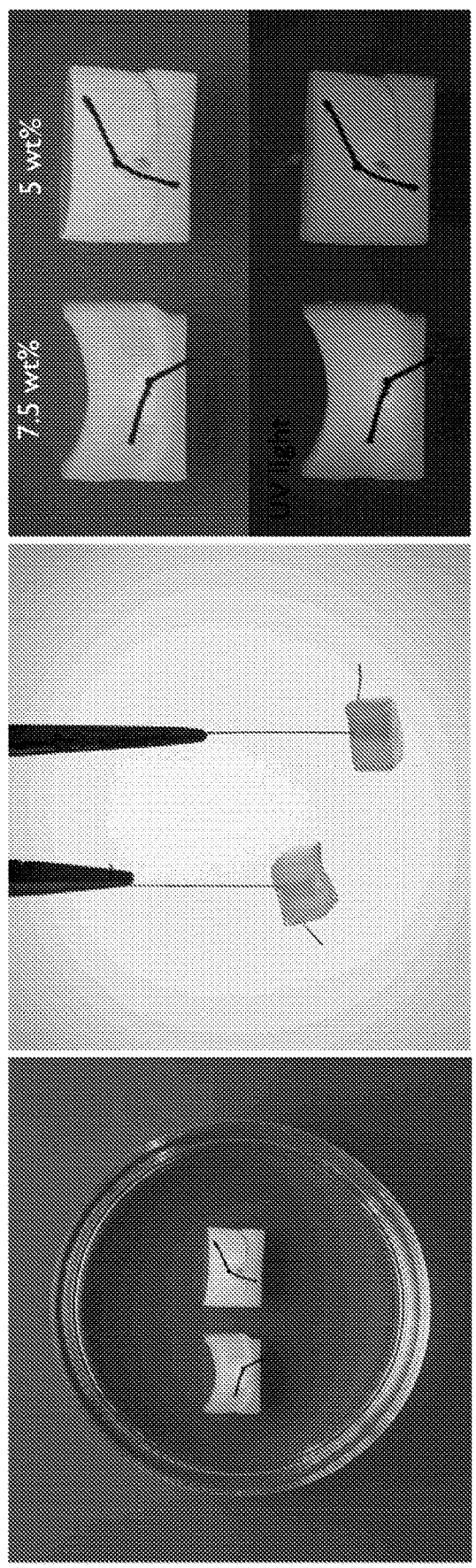
FIG. 10 depicts still images of sutured constructs using either 5 wt % gelatin as the hydrogel matrix or 7.5 wt %.
Figure 10:
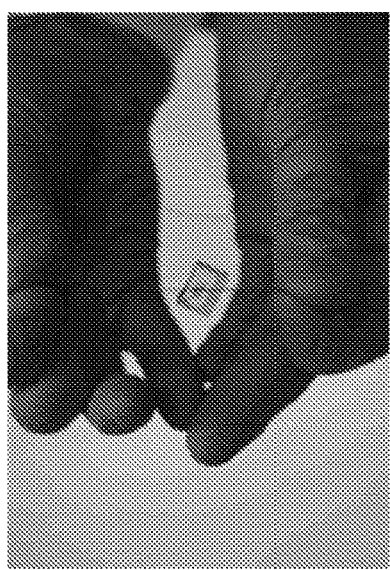

FIG. 9 depicts: (A) Confocal images of longitudinal cross-sections for endothelial marker expression in construct matured for 4 weeks in two different extracellular matrix compositions with (left panels) or without (right panels) fully printed wall structures. RFP-HUVECs do not perform as well and can be replaced with 'normal' HUVEC cells not expressing a fluorescent marker; and (B) Confocal images of longitudinal and horizontal cross-sections for medial marker expression in construct matured for 4 weeks in two different extracellular matrix compositions. Smooth muscle cells express specific markers for up to 4 weeks of culture time.

3. Histological Staining

To perform histological staining the samples needed to be cryosectioned. For this, a small piece of sample was incubated overnight in TissueTek OCT to ensure proper penetration of the freezing medium into the hydrogel, where significant shrinkage of the construct occurred and frozen the next day using the Peltier element in the cryostat. This rather slow process was found to be ideal in freezing hydrogels, faster methods often introduced cracks. Frozen sections were made with a thickness in the range of 30-40 µm and stored at −20° C. For Hematoxylin and Eosin (H&E) staining (Cardiff R D, Miller C H, Munn R J. Manual Hematoxylin and Eosin Staining of Mouse Tissue Sections. *Cold Spring Harb Protoc.* 2014; 2014(6)), sections were immersed in water for 30 s to remove residual salts and buffers. Then, the slide was dipped into a Coplin jar containing Mayer's hematoxylin and agitated for 30 s. The staining solution was rinsed off in water for 1 min. This step was repeated once to achieve optimal staining. Subsequently, the section was stained with 1% Eosin staining solution for 30 s. Afterwards, sections were dehydrated with two changes of 95% ethanol and two changes of 100% ethanol for 30 s each. The alcohol was extracted by two changes of xylene and the section was mounted in DPX resinous mountant with a cover glass on top of the section.

Figure 7:
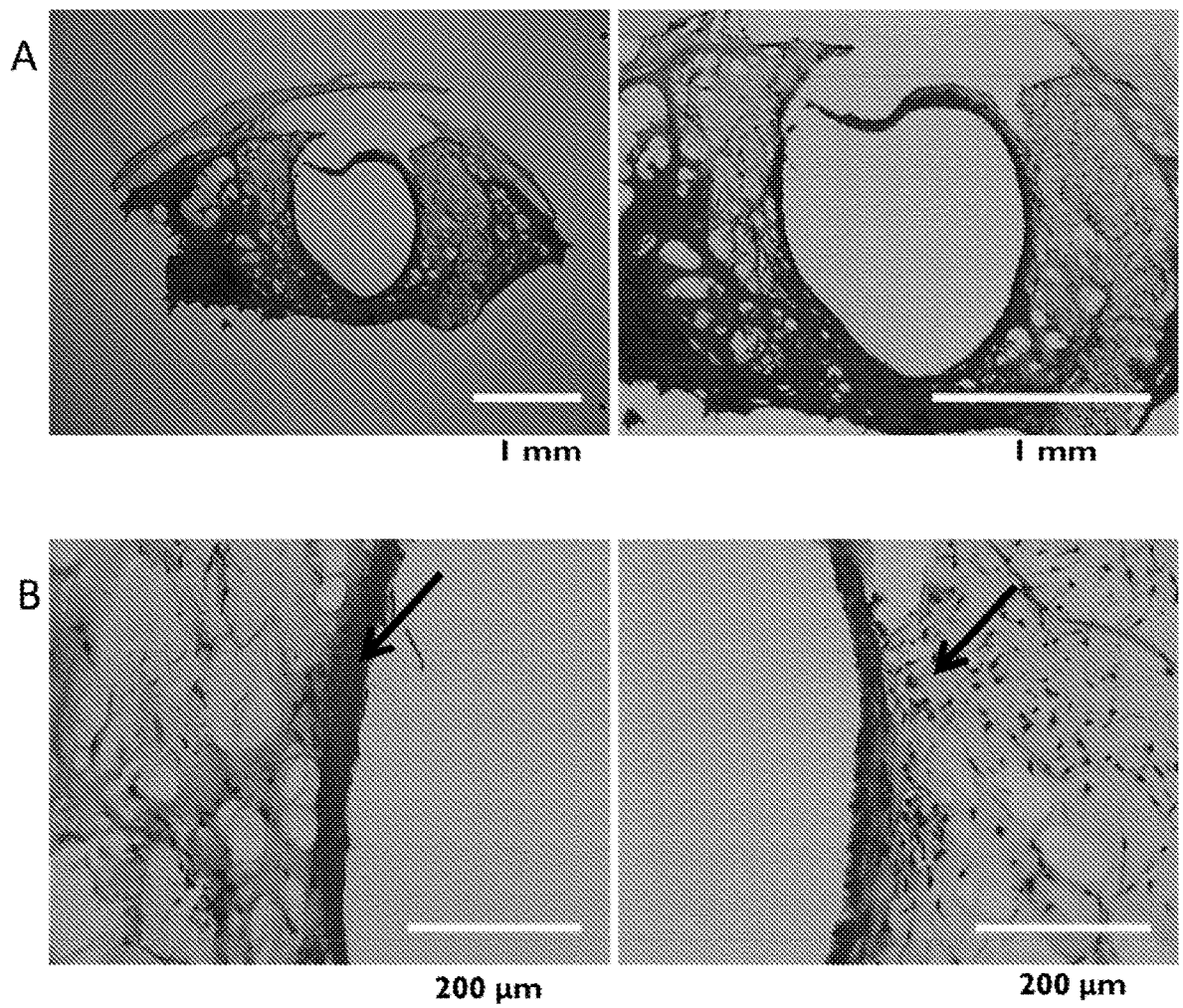
FIG. 7 depicts images showing matrix remodeling: (A) Hematoxylin and Eosin (H&E) stained cryosections of a construct matured for 2 weeks under active perfusion; and (B) Detail images of (A) with arrow pointing to dense protein deposition by the cells close to the lumen resembling native extracellular matrix. As shown in (B), cells remodel the matrix and start lying down their own ECM.

FIG. 7 illustrates: (A) Hematoxylin and Eosin (H&E) stained cryosections of a construct matured for 2 weeks under active perfusion; and (B) Detail images of (A) with arrow pointing to dense protein deposition by the cells lose to the lumen resembling native extracellular matrix.

4. Flow Cytometry

To determine proliferation of the different cell types in the printed construct, cells were subjected to flow cytometry analysis at day 1, day 4 and day 7 after printing. For flow cytometry analysis of cell numbers in the different layers of the printed constructs, the constructs needed to be dissociated and the cells isolated. Three samples per time point were dissociated and individually collected. Protocols for dissociation were adopted from Homan et al. A dissociation solution comprising of 0.5% trypsin and 10 mM EDTA was made. The solution was adjusted to pH 8 and equilibrated in a cell culture incubator for 1 h. Three constructs were taken out of the incubator per time point, the chips were disassembled and the hydrogel construct taken out of the gasket. The sample was cut open longitudinally, and any residual gel matrix not containing cells was removed using a sterile scalpel blade. These strips were then washed in PBS and incubated for 30 min in the dissociation solution at room temperature. Detachment of cells was controlled visually under a microscope during this incubation time. After incubation, strips were removed, detached cells were concentrated by centrifugation for 5 min at 220 g, and resuspended in 50 µL of PBS. Cells were fixed by addition of 500 µL of formalin and subsequently washed two times in PBS. Before flow cytometry, cells were stained with DAPI (1:1000) for 5 min. The samples were analyzed by a flow cytometer counting 10000 cells for each sample (BD Ariall1). Data analysis was performed in FlowJo and GraphPad Prism.

FIG. 8A shows layer-specific proliferation of the different cell types in the system was analyzed via flow cytometric analysis, a p-value below 0.05 was considered statistically significant.

5. Distensibility Measurements

To investigate vessel wall behavior and remodeling over time, constructs were subjected to distensibility measurements and subsequent fixation (see above) with 3 samples each on day 1, day 4, day 7, and day 14 after printing. The samples were equilibrated to room temperature for 1 hour and the open lumen was filled with water. Since this measurement was conducted to investigate mechanical behavior of the vessel wall over time, cellular survival was neglected. The chip inlet tubing and reservoir of each sample was removed, the chip was mounted on the stage of a digital Keyence microscope, and the inlet perfusion pin was connected to a long piece of tubing (Versilic) containing water. The outlet tubing was clipped and the long tubing at the inlet was used to apply hydrostatic pressure. After equilibration of the system, the diameter of the vessel was measured via the microscope's software. The values were recorded and used for subsequent analysis. The data was processed using Excel and Prism.

6. Preliminary Suture Testing

After long-term perfusion (4 weeks), the constructs were taken out of perfusion and cut in half. One half was fixed and the other one was cut into 5-8 mm thick pieces with a weight of ~500 mg each. A silk suture was threaded through the vessel from the inside out and a simple knot tied to determine stability of the construct. The thus sutured construct was mounted via the thread. Additional hose clamps may be hung from the silk thread for additional weight.

FIG. 10 shows images from suturability testing as well as still images of sutured constructs.

7. Image Analysis

To determine the orientation and alignment of the cell-layers directly below the endothelium, the samples were fixed and stained (see above) and imaging was performed on vessels cut open along their long axis to expose the inner part of the channels.

At least 4 images of each half vessel per sample and 3 samples per group were taken, unless otherwise stated. Images were cropped to the inner vessel wall and rotated to align with flow direction (0°, circumferential alignment 90°). OrientationJ Analysis (FIJI) was run on Finite Difference Gradient mode (vessels) and on Fourier gradient mode (cast controls), and the angle alignment distribution data was exported to Excel. This distinction was necessary to avoid picking up background staining of the endothelial cells over the brighter SMCs and HNDFs in the vessel analysis, which would have falsified the information. In the cast controls, this distinction is not favorable, since the only difference in intensity of staining comes from depth in the gel and no endothelium needs to be eliminated. Since + or −45° angles do not need to be discriminated, observations for angles with the same absolute value were added up. For 0° and 90° the one available value available was doubled. Subsequently, the distribution was normalized to the total number of observations (100 total observations per image). All images per sample were averaged (technical replicates) and then the samples in each group were averaged (biological replicates).

The shown standard deviation is calculated from the biological replicates neglecting the technical replicate differences.

FIG. 8C depicts alignment analysis of the sub-endothelial layer of cells. Alignment was analyzed via the OrientationJ Plugin in ImageJ and 6 different frames of upper or lower longitudinal section were analyzed per sample.

8. Statistical Analysis

Statistical analysis was performed in GraphPad Prism 5. Generally, a p-value of <0.05 was considered to indicate a statistically significant difference between means. For comparison of experimental groups of the cell viability analysis via live/dead cell staining, and the flow cytometry data, an ANOVA with Tukey's post-test with a significance level of 0.05 was performed to determine statistical differences between groups. For the MTS assay testing cell culture medium compatibility, a two-way ANOVA with a Bonferroni's post-test was performed to determine statistical differences between the medium treatments.

9. Contractility Measurement

For analysis of biological responsivity or vasoactivity of the printed blood vessel, the constructs were matured for 2/4 weeks under active perfusion and used for live analysis. To assess contractile behavior the resistance to flow was measured by measuring volumetric flowrate under increasing hydrostatic pressure. Volumetric flow was measured by weighing out the collective flow through the construct after 30 s of flow at a given pressure. Resistance to flow could then be calculated. All measurements were conducted using HEPES-buffered Tyrode's solution. For contractility measurements, Tyrode's solution was supplemented with increasing concentrations of Norepinephrine (0.1 nM to 10 µM) and resistance to flow was measured as mentioned above (data not shown).

10. Calcium Imaging

In order to determine responsivity to vasoactive compounds, the printed blood vessels were matured for 2/4 weeks under active perfusion and used for live staining with a calcium dye, rhod-2 AM. The constructs were taken out of their housing live and cut into 3-5 mm thick tissue sections. The thus produced samples were washed and loaded with the dye at 10 µM concentration in calcium free cell culture medium. After loading for 45 min at 37° C. and 5% $CO_2$, the samples were washed 3 times with calcium free PBS and kept alive in warm serum free cell culture medium until the measurement started. Baseline fluorescence without stimulation was assessed with a scanning laser confocal microscope as mentioned above in times series mode. After acquisition of the baseline fluorescence, the samples were stimulated with a pulse of 10 µM Norepinephrine and changes in fluorescence were recorded under the same settings as the baseline fluorescence for 3-5 min. Calcium traces were collected from the intensity information of an average of 20 pixels per image over the course of the experiment and analyzed using GraphPad Prism.

Figure 11A:
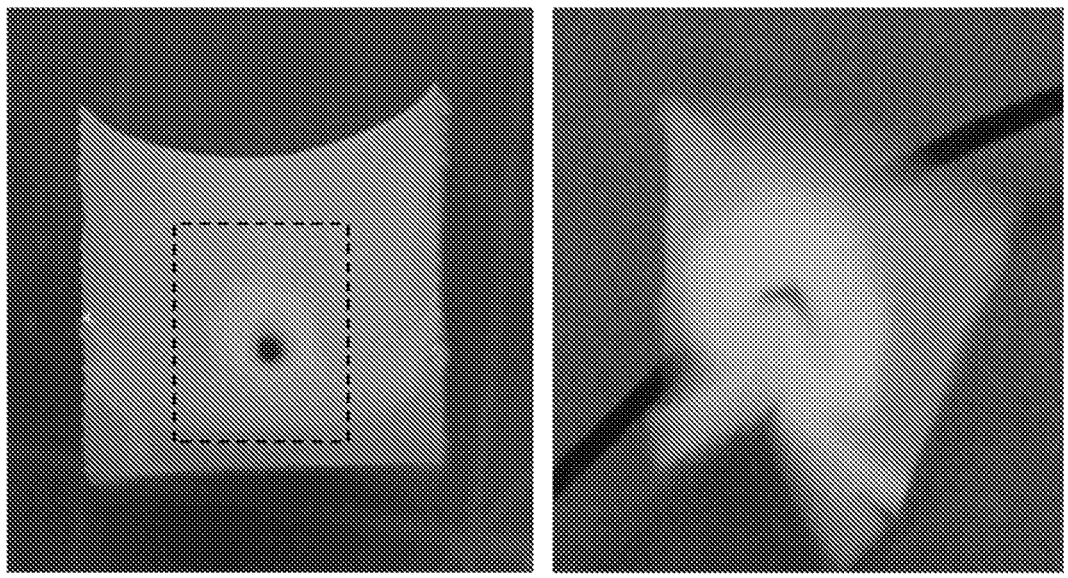
FIG. 11A depicts images of a sutured vessel part before and after cutting away the surrounding hydrogel (gelatin might be restraining but the smooth muscle cells exhibit physiological calcium traces).
Figure 11B:
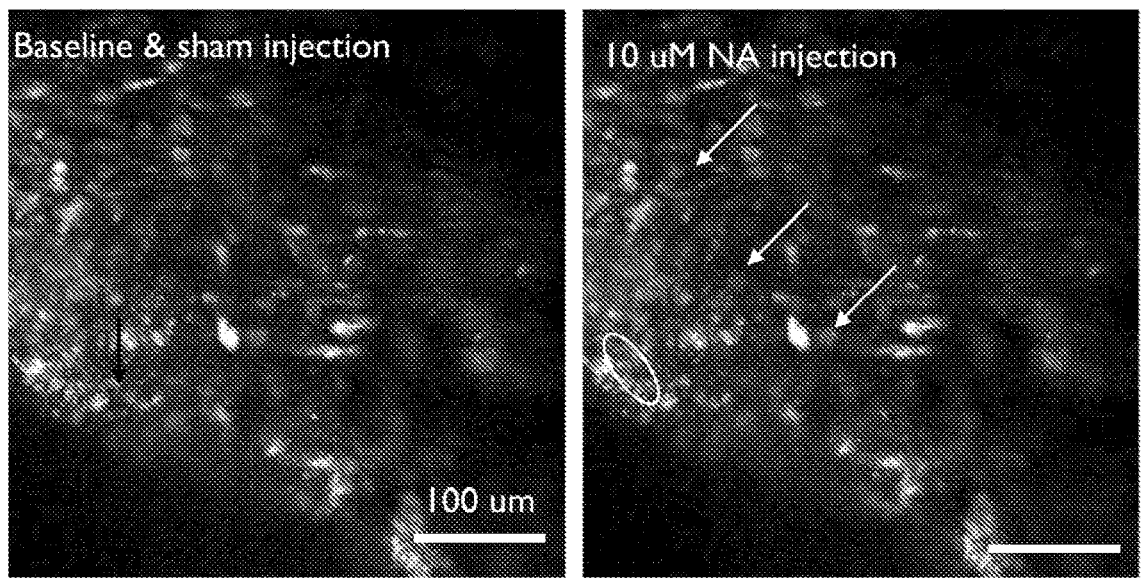
FIG. 11B depicts: still images from time series videos of calcium imaging data (Rhod-2 AM dye) of baseline fluorescence and norepinephrine (NA) injection; the arrows and the oval correspond to the extracted calcium traces (top figure); and calcium transient measurements after 2 weeks where traces are obtained from image analysis of the time series; the arrow points to the time point of injecting 10 µM norepinephrine.
Figure 11B:
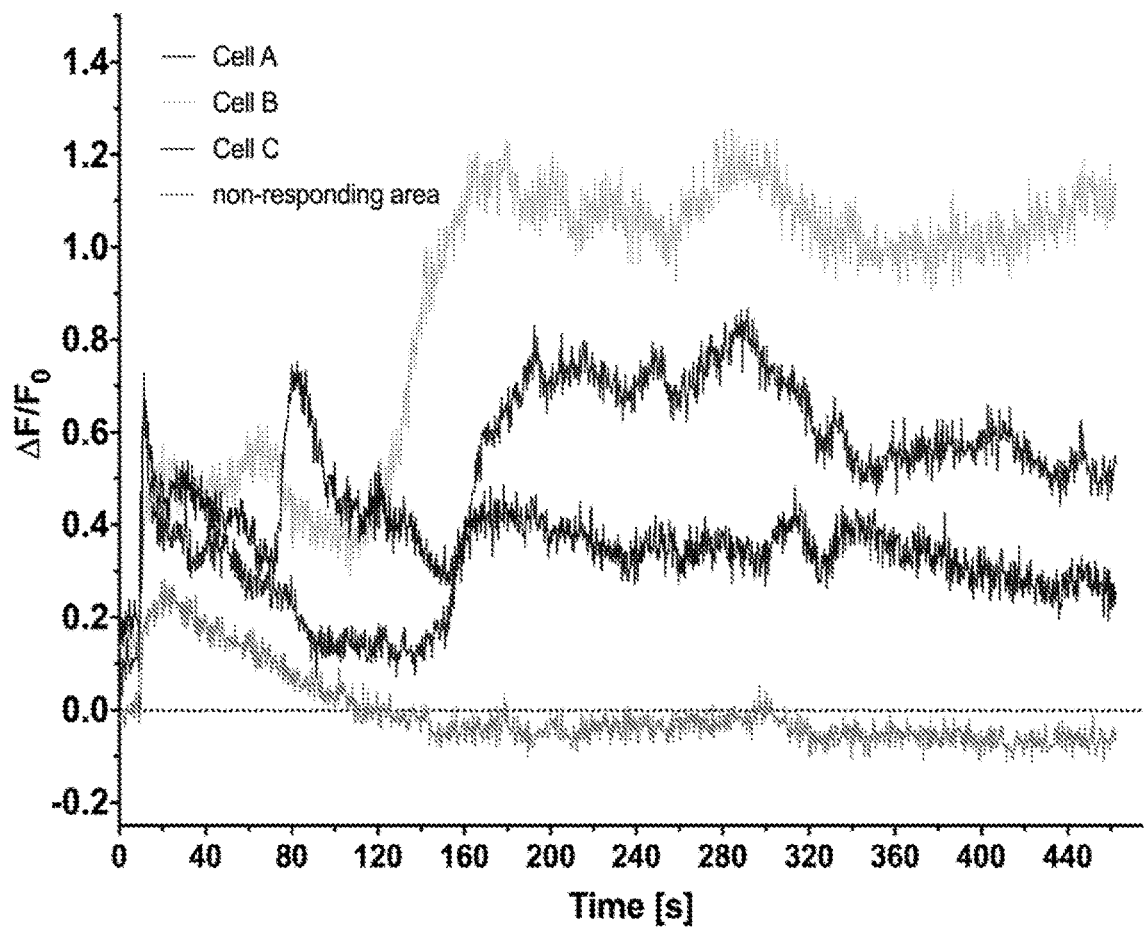

FIG. 11A shows images of a sutured vessel part before and after cutting away the surrounding hydrogel. FIG. 11B shows stills from time series videos of calcium imaging data (Rhod-2 AM dye) of baseline fluorescence and norepinephrine (NA) injection (top figure): the arrows and the oval correspond to the calcium traces in the bottom figure. The bottom of FIG. 11B shows calcium traces obtained from image analysis of the time series acquired in, the black arrow points to the time point of injecting 10 uM norepinephrine.

11. Variable Cell Lines for SMC Layer

To test whether vessel maturation is affected by changes in primary cell line used in the printing process, an additional cell type, aortic smooth muscle cells (AoSMCs) were used instead of the human umbilical artery SMCs mentioned earlier. All other parameters were kept constant.

12. Vascular Permeability

To test diffusion of albumin-bound EvansBlue from the main lumen into the matrix in conditions of the printed vessel with or without endothelial cells (seeded into the lumen to form the intimal layer of the vessel), the dye Evans-Blue was supplied at a concentration of 0.05% in the perfusing cell culture medium for 2.5 h.

For measuring how much dye extravasated in the two conditions (4-5 vessels per condition), the vessel was flushed once with phosphate-buffered saline and each vessel was cut into 5 pieces of 5 mm thickness. Subsequently, the dye was extracted via formamide extraction for 2 days at room temperature and the amount of dye was measured colorimetrically by absorbance measurement at 630 nm wavelength. The amount of dye measured was normalized by weight surface area of the vessel piece.

As shown in FIG. 13, the seeded endothelium in the in vitro vessels serves as a diffusional barrier for molecules like albumin of ~66 kDa as it does in vivo.

Example 2: Prophetic Examples of Possible Read-Outs

1. Calcium Imaging with Electrical Stimulation

Expanding on the stimulation techniques for assessing vasoactivity (vaso-contraction or dilation) of the printed blood vessel construct, various other compounds like endothelin-1, nitric oxide, or histamine can be tested in the setup for the calcium imaging that is mentioned above. In addition, a more generic stimulus can be applied. Smooth muscle cells are responsive to electrical stimulation and a testbed is being developed, in which electrical field stimulation can be applied while like calcium imaging is performed. In addition, the diameter of the blood vessel section can be monitored via brightfield microscopy during the stimulation. Alternatively, the vessel's contractile ability could be stimulated via biological agents like noradrenaline or endothelin-1.

2. Mechanical Testing

Testing tissue mechanics after maturation will include quantitative suturability testing and burst pressure measurements. In addition, cellular remodeling of the matrix can be measured via changes in modulus of the tissue over time. This data will then be used in modelling the mechanics of the tissue surrounded by matrix and predict the possible distention (contraction/relaxation) of the tissue. Consequently, from these analyses, the force generated by the cells under this current maturation regime will be calculated.

REFERENCES

Homan K A, Kolesky D B, Skylar-Scott M A, et al. Bioprinting of 3D Convoluted Renal Proximal Tubules on Perfusable Chips. *Sci Rep.* 2016; 6:34845. doi: 10.1038/srep34845

Kolesky D B, Truby R L, Gladman A S, Busbee T A, Homan K A, Lewis J A. 3D bioprinting of vascularized, heterogeneous cell-laden tissue constructs. *Adv Mater.* 2014; 26(19):3124-3130. doi: 10.1002/adma.201305506.

Kolesky D B, Homan K A, Skylar-Scott M A, Lewis J A. Three-dimensional bioprinting of thick vascularized tissues. *Proc Natl Acad Sci USA.* 2016; 113(12):3179-3184. doi: 10.1073/pnas. 1521342113.

Lorang D J, Tanaka D, Spadaccini C M, Rose K A, Cherepy N J, Lewis J A. Photocurable liquid core-fugitive shell printing of optical waveguides. *Adv Mater.* 2011; 23(43): 5055-5058. doi: 10.1002/adma.201102411.

Frutiger A, Muth J T, Vogt D M, et al. Capacitive soft strain sensors via multicore-shell fiber printing. *Adv Mater.* 2015; 27(15):2440-2446. doi: 10.1002/adma.201500072.

Throughout this specification, various indications have been given as to preferred and alternative embodiments of the invention. However, the foregoing detailed description is to be regarded as illustrative rather than limiting and the invention is not limited to any one of the provided embodiments. It should be understood that it is the appended claims, including all equivalents, are intended to define the spirit and scope of this invention.

The invention claimed is:

1. A method of producing a perfusable multi-layered tubular tissue construct, comprising:
    depositing on a substrate one or more cell-laden filaments, each cell-laden filament comprising:
        a plurality of concentric and coaxial cell-laden ink layers, each cell-laden ink layer comprising one or more predetermined cell types and extending at least a portion of the length of the cell-laden filament, wherein the one or more predetermined cell types are cell aggregates or clusters of cells, and
        a core comprising a fugitive ink, wherein the fugitive ink serves as a template for an open perfusable lumen within the cell-laden filament;
    removing the fugitive ink to create the open perfusable lumen;
    seeding the lumen with endothelial cells by:
        providing the endothelial cells with the fugitive ink, wherein the endothelial cells remain in the open perfusable lumen after the fugitive ink is removed; and/or
        injecting a suspension of endothelial cells into the open perfusable lumen after removing the fugitive ink; and
    exposing the one or more cell-laden filaments to fluid perfusion to induce cell proliferation and development, thereby producing the perfusable multi-layered tubular tissue construct.

2. The method of claim 1, wherein the step of depositing on a substrate one or more cell-laden filaments comprises:
    flowing the fugitive ink through a first extrusion tube;
    flowing a first cell-laden ink comprising one or more predetermined cell types through a second extrusion tube overlaying the first extrusion tube, the first cell-laden ink flowing around and enclosing the fugitive ink;
    flowing a second cell-laden ink comprising one or more predetermined cell types through a third extrusion tube overlaying the second extrusion tube, the second cell-laden ink flowing around and enclosing the first cell-laden ink,
    thereby forming the core comprising the fugitive ink surrounded by an inner layer comprising a first cell-laden ink layer and an outer layer comprising a second cell-laden ink layer.

3. The method of claim 2, further comprising providing an extrusion head including the first, second, and third extrusion tubes arranged in a concentric configuration, wherein the extrusion head is moved relative to the substrate during the flowing of the fugitive ink, the first and the second cell-laden inks, the cell-laden filament being deposited on the substrate in a predetermined configuration.

4. The method of claim 1, wherein each cell-laden ink comprises a different type of viable cells.

5. The method of claim 1, wherein each cell-laden ink comprises overlapping populations of viable cells.

6. The method of claim 1, wherein the cell types are selected from the group consisting of smooth muscle cells, mesenchymal cells, pericytes, endothelial cells, and epithelial cells.

7. The method of claim 2, wherein the first cell-laden ink comprises smooth muscle cells and the second cell-laden ink comprises fibroblast cells.

8. The method of claim 1, wherein the cell-laden ink layers form a medial layer and an adventitial layer of a blood vessel.

9. The method of claim 1, wherein the perfusable multi-layered tubular construct is a printed blood vessel.

10. The method of claim 1, wherein the multi-layered tubular construct is a branched multi-layered tubular construct.

11. The method of claim 1, further comprising at least partially surrounding the one or more cell-laden filaments with an extracellular matrix composition, wherein the extracellular matrix composition comprises one or more of gelatin, fibrin, fibrinogen, transglutaminase, thrombin and gelatin methacrylate, collagen, collagen-acrylate, a solubilized basement membrane matrix secreted by Engelbreth-Holm-Swarm (EHS) mouse sarcoma cells, poly lactic-co-glycolic acid (PLGA), alginate, or chitosan.

12. The method of claim 11, further comprising depositing one or more sacrificial filaments on the substrate prior to at least partially surrounding the one or more cell-laden filaments with the extracellular matrix composition to form a sacrificial filament network interpenetrating the one or more cell-laden filaments, each of the sacrificial filaments comprising a fugitive ink.

13. The method of claim 12, wherein the network comprises flow channels in fluid communication with the cell-laden filaments for perfusion thereof after removal of the fugitive ink.

14. The method of claim 1,
wherein:
    the cell-laden filaments comprise one or more functional chemical substances selected from the group consisting of: drugs, small molecules, toxins, proteins, growth factors, and hormones; and/or
    each of the cell-laden ink layers comprises a cell concentration of from one cell/ml to about $10^9$ cells/ml; and/or
    the cell concentration is uniform throughout each of the cell-laden ink layers.

15. The method of claim 1, wherein the step of exposing the one or more cell-laden filaments to fluid perfusion is under a fluid shear stress (FSS).

16. The method of claim 15, wherein the FSS is pulsed to mimic blood pressure changes during regular heart beats.

17. The method of claim 1, wherein:
    the substrate is plastic, glass, or a solubilized basement membrane matrix secreted by Engelbreth-Holm-Swarm (EHS) mouse sarcoma cells, and
    optionally, the substrate is plasma treated or coated with a layer of at least one of a solubilized basement membrane matrix secreted by Engelbreth-Holm-Swarm (EHS) mouse sarcoma cells, poly L-lysine, gelatin, fibrin, fibrinogen, nitogen, vitrogen, collage I, collagen IV, chitosan, alginate, glycosaminoglycans, or other biomaterial.

18. The method of claim 1, wherein the cell-laden ink layers all have varying thickness.

19. The method of claim 1, wherein each cell-laden filament further comprises one or more concentric and coaxial non-cellular fugitive ink layer.

20. The method of claim 19, wherein the non-cellular fugitive ink layers comprise one or more materials that impart mechanical stability to the perfusable multi-layered tissue construct.

21. The method of claim 1, wherein each cell-laden filament further comprises one or more concentric and coaxial layer comprising growth factors.

22. A perfusable multi-layered tubular tissue construct produced by the method of claim 1.

23. The perfusable multi-layered tubular tissue construct of claim 22, wherein the tubular structure is selected from the group consisting of an artery, an arteriole, a small scale vessel, and a vein.

24. A method of producing a blood vessel construct, comprising:
   depositing on a substrate one or more filaments, each filament comprising: a first cell-laden ink layer and a second cell-laden ink layer, the first and the second cell-laden layers being concentric and extending at least a portion of the length of the filament, the first cell-laden ink layer comprising a smooth-muscle cell (SMC)-containing cell-laden ink and the second cell-laden ink layer comprising a fibroblast-containing cell laden ink, and within the cell-laden ink layers a core comprising a fugitive ink, wherein the fugitive ink serves as a template for an open perfusable lumen within the filament;
   removing the fugitive ink to create the open perfusable lumen;
   after removing the fugitive ink, injecting a suspension of endothelial cells into the open perfusable lumen; and
   exposing the one or more filaments to fluid perfusion to induce cell proliferation and maturation thereby producing the blood vessel construct.

25. A kit comprising:
   the printed multi-layered tubular construct of claim 23;
   hardware for chip assembly; and
   instructional materials.

* * * * *